(12) United States Patent
Egerström et al.

(10) Patent No.: US 10,342,932 B2
(45) Date of Patent: Jul. 9, 2019

(54) MEDICAMENT DELIVERY DEVICE

(71) Applicant: Carebay Europe Ltd, Swatar (MT)

(72) Inventors: Johan Egerström, Saltsjö-Boo (SE);
Marcus Söderlund, Stockholm (SE);
Nils Ronquist, Stockholm (SE)

(73) Assignee: SHL MEDICAL AG, Zug (CH)

( * ) Notice: Subject to any disclaimer, the term of this patent is extended or adjusted under 35 U.S.C. 154(b) by 1016 days.

(21) Appl. No.: 14/760,872

(22) PCT Filed: Jan. 14, 2014

(86) PCT No.: PCT/EP2014/050570
§ 371 (c)(1),
(2) Date: Jul. 14, 2015

(87) PCT Pub. No.: WO2014/111371
PCT Pub. Date: Jul. 24, 2014

(65) Prior Publication Data
US 2015/0359978 A1    Dec. 17, 2015

Related U.S. Application Data

(60) Provisional application No. 61/752,606, filed on Jan. 15, 2013.

(30) Foreign Application Priority Data

Jan. 15, 2013  (SE) ...................... 1350047

(51) Int. Cl.
*A61M 15/00*  (2006.01)
*A61M 15/06*  (2006.01)
(Continued)

(52) U.S. Cl.
CPC ........ *A61M 11/001* (2014.02); *A61M 5/2033* (2013.01); *A61M 5/315* (2013.01);
(Continued)

(58) Field of Classification Search
CPC ............ A61M 13/00; A61M 2205/183; A61M 2205/44
See application file for complete search history.

(56) References Cited

U.S. PATENT DOCUMENTS 1,897,343  A  *  2/1933  Stephenson ........... A61M 15/00
                                              128/200.12
5,137,516  A     8/1992  Rand et al.
(Continued)

FOREIGN PATENT DOCUMENTS

WO    2006/126902 A1    11/2006
WO    2011/039236 A1    4/2011

OTHER PUBLICATIONS

EPO, Int'l Search Report in PCT/EP2014/050570, dated Apr. 22, 2014.
EPO, Written Opinion in PCT/EP2014/050570, dated Apr. 22, 2014.

*Primary Examiner* — Peter S Vasat
*Assistant Examiner* — Ned T Heffner
(74) *Attorney, Agent, or Firm* — McDonnell Boehnen Hulbert & Berghoff LLP

(57) ABSTRACT

A metered droplet medicament delivery device for delivering metered doses of medicament includes a proximal part and a distal part having opposite distal and proximal ends; a medicament container with a movable stopper; and a dose delivery mechanism that includes a plunger rod, operably arranged to act on the stopper. The proximal and distal parts are releasably connectable to each other. The proximal part includes a medicament container holder accommodating the medicament container, and the distal part includes the dose delivery mechanism. A plunger rod positioning member is engageable with a proximal end of the plunger rod and with a proximal area of the distal part for positioning the plunger rod in a longitudinal direction in relation to the proximal area.

19 Claims, 20 Drawing Sheets

(51) Int. Cl.
*A61M 11/00* (2006.01)
*A61M 5/31* (2006.01)
*A61M 5/315* (2006.01)
*A61M 11/06* (2006.01)
*A61M 5/20* (2006.01)
*A61M 5/24* (2006.01)
*A61M 5/14* (2006.01)

(52) U.S. Cl.
CPC ...... *A61M 5/3146* (2013.01); *A61M 5/31515* (2013.01); *A61M 5/31535* (2013.01); *A61M 5/31553* (2013.01); *A61M 11/007* (2014.02); *A61M 11/06* (2013.01); *A61M 15/0025* (2014.02); *A61M 15/0065* (2013.01); *A61M 5/3156* (2013.01); *A61M 5/31583* (2013.01); *A61M 2005/1402* (2013.01); *A61M 2005/202* (2013.01); *A61M 2005/2073* (2013.01); *A61M 2005/2485* (2013.01); *A61M 2005/3142* (2013.01); *A61M 2205/073* (2013.01); *A61M 2205/276* (2013.01); *A61M 2205/3379* (2013.01); *A61M 2210/0612* (2013.01)

(56) References Cited

U.S. PATENT DOCUMENTS

| | | | |
|---|---|---|---|
| 2009/0293870 A1* | 12/2009 | Brunnberg | A61M 5/31551 128/203.12 |
| 2011/0224622 A1 | 9/2011 | Karlsson | |
| 2011/0245780 A1 | 10/2011 | Helmer et al. | |
| 2012/0136306 A1 | 5/2012 | Bartha | |
| 2012/0216805 A1 | 8/2012 | Brunnberg et al. | |

* cited by examiner

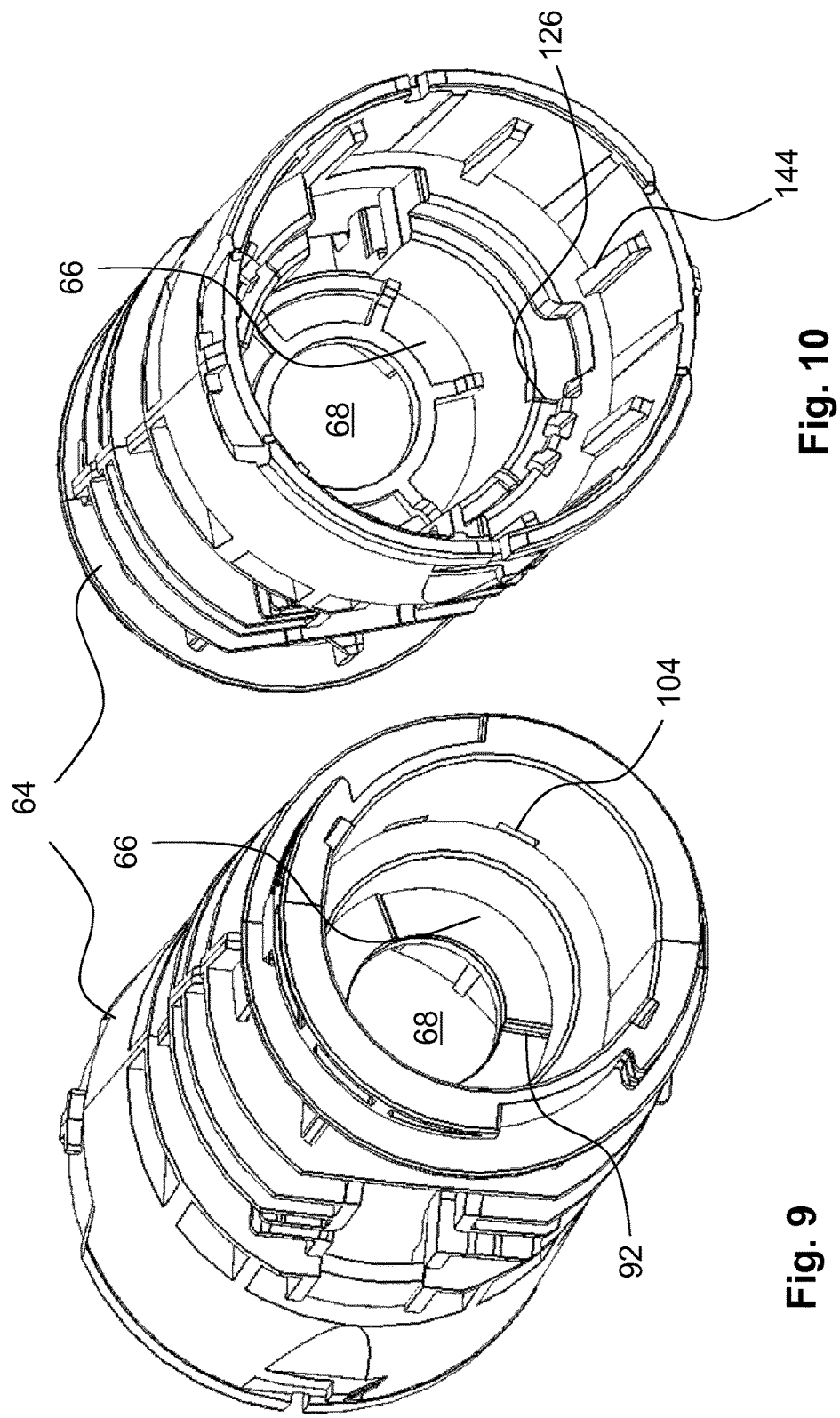

MEDICAMENT DELIVERY DEVICE

TECHNICAL AREA

The present invention relates to a medicament delivery device and in particular a device capable of delivering a number of predetermined metered doses.

BACKGROUND OF INVENTION

For a number of years, medicament delivery devices have been developed, which contain a medicament container provided with a stopper arranged movable inside the container for delivering doses of medicament. The stopper is usually moved by an elongated plunger rod, the plunger rod is in turn often drivably connected to a force mechanism, such as spring force members, capable of accumulating energy for driving the plunger rod when released.

With many devices, a medicament container is placed inside one housing part of the device, while the drive mechanism, comprising the plunger rod, is arranged in another housing part. The device is then assembled in that the housing parts are connected to each other to make the device ready for delivery of a dose of medicament. Usually a proximal end of the plunger rod is, during the connection, brought in contact with a distally directed surface of the stopper. Before connection, the plunger rod is often brought manually to a position that theoretically will ensure a contact with the stopper after assembly. The same situation may also occur when a device has been used such that the medicament container has been emptied. When a new, full medicament container is to replace the empty container, the plunger rod is in its most proximal position and has to be brought to its initial position.

However, medicament containers tend to have quite a large tolerance range in the longitudinal direction, i.e. the actual length of a certain type of medicament container may vary within a span of several millimeters. Also the actual position of the stopper in the longitudinal direction of a new and unused medicament container may vary within quite a large span. These tolerance ranges may in total lead to a gap between the plunger rod and the stopper when the device has been assembled. In turn, this gap will lead to a delivered first dose that is smaller than the preset, intended dose because the plunger rod moves a certain distance during its delivery stroke without moving the stopper.

Because of the tolerance ranges, it is further difficult to provide a fixed stop for the plunger rod at the initial position, because either there will be a gap or the stopper will be pressed and deformed against the plunger rod, which may lead to difficulties in assembling the housing parts and/or that a large pressure is built up inside the medicament container or in the flexible stopper, which may lead to leakage or premature dose delivery.

US 2011/0245780 discloses a medicament delivery device comprising an adjustment mechanism for handling or adjusting an end surface of a plunger rod in relation to a stopper inside a medicament container. The adjustment mechanism comprises an adjustment member threadedly engaging an end of the plunger rod such that rotation of the adjustment member will cause it to move in the longitudinal direction in relation to the plunger rod, whereby an end surface of the engagement member will contact the stopper.

One drawback with the solution according to US 2011/0245780 is that it is difficult to know beforehand where to position the adjustment member in relation to the plunger rod for a certain medicament container. It would therefore be necessary to adjust and try the connection between the plunger rod and the medicament container a number times in order to eventually find the appropriate position with contact between the plunger rod and the stopper but without any force from the plunger rod on the stopper.

There is thus still a need for devices where it is ascertained that there is an initial positive contact between a plunger rod and a stopper of a medicament container before an initial dose delivery.

BRIEF DESCRIPTION OF INVENTION

As used herein, the term "liquid" encompasses all solutions, suspensions, emulsions, oils, gels and so forth, which generally behave as liquids at operating temperatures.

The term explicitly includes solid compositions dissolved or dispersed in a liquid carrier. Materials behaving as highly viscous liquids are also included.

In the present application, when the term "distal part/end" is used, this refers to the part/end of the medical delivery device, or the parts/ends of the members thereof, which during use of the device is located the furthest away from the delivery site of the patient. Correspondingly, when the term "proximal part/end" is used, this refers to the part/end of the device, or the parts/ends of the members thereof, which under use of the device is located closest to the delivery site of the patient.

The aim of the present invention is to remedy the drawbacks of the state of the art devices. This is obtained by a medicament delivery device according to the features of the independent patent claim 1. Preferable embodiments of the invention form the subject of the dependent patent claims.

According to the present invention, a medicament delivery device for delivering metered doses of medicament is provided. The device comprises a generally elongated body comprising a proximal and a distal part having opposite distal and proximal ends and a compartment inside said body, capable of accommodating a medicament container. The medicament container is arranged with a movable stopper. The medicament delivery device may also comprise a dose delivery mechanism, which in turn comprises a plunger rod, operably arranged to act on said stopper.

According to a preferable embodiment of the invention, the proximal part and the distal part are releasably connectable to each other. This facilitates insertion of a medicament container, whereby the proximal part comprises the compartment for accommodating the medicament container. Also, the distal part comprises said dose delivery mechanism with said plunger rod.

According to the present invention, there is provided a plunger rod positioning member. It may be engageable with a proximal end of the plunger rod as well as engageable with a proximal area of the distal part. This enables the positioning of the plunger rod in a longitudinal direction of the device in relation to the proximal area by displacing the plunger rod distally using the positioning member until the positioning member connects with the proximal end of the distal part.

Thereby, the plunger rod is positioned appropriately when the proximal part with the medicament container is to be connected to the distal part. When positioned, the plunger rod protrudes a predetermined distance from the proximal end of the distal part, which distance is chosen such that it is ascertained that all tolerance variations of the medicament container, and the variations in actual position of the stopper inside a full medicament container are handled such that the proximal end of the plunger rod is always in contact with the distal end surface of the stopper when the proximal part with the medicament container, is connected to the distal part. This eliminates the risk that the first delivered dose from a new medicament container is not a full dose due to that the plunger rod was not in initial contact with the stopper.

According to a preferable embodiment, the plunger rod positioning member is arranged removable from said distal part after adjustment of said plunger rod such that the proximal part can be attached. The medicament delivery device may then be arranged with an attachment area where the plunger rod positioning member may be attached until a subsequent positioning procedure. The attachment area may for example be at a distal end of the device.

Preferably, the plunger rod positioning member may comprise a seat for the proximal end of said plunger rod as well as a contact surface for contact with said distal part. In this manner, precisely defined reference surfaces are obtained, in turn providing a well-defined position of the plunger rod in relation to the distal part when the plunger rod positioning member has been utilized.

The device may further be provided first holding members on said plunger rod positioning member cooperating with corresponding second holding members on said distal part for releasably holding said plunger rod positioning member. The plunger rod positioning member may thus also be used as a transport cover, which protects the plunger rod and the proximal end of the distal part. The holding members reduce the risk of the plunger rod positioning member falling off the distal part. Alternatively the holding members could be replaced by a push-fit connection between the plunger rod positioning member and the distal part.

The dose delivery mechanism may further comprise a plunger rod guide member arranged in a rotationally locked relation with said plunger rod as well as a drive nut threadedly connected to said plunger rod, wherein said plunger rod guide member is rotatably arranged in said distal part such that said plunger rod may rotate, and thereby move in the distal direction when in engagement with said plunger rod positioning member, i.e. when the distal part is detached from the proximal part.

Also, the distal part may preferably comprise a plunger rod guide member lock capable of rotationally locking said plunger rod guide member in relation to the distal part when said distal and said proximal parts are connected to each other.

According to a further aspect of the invention the medicament delivery device is an inhalation device, an eye spray device or an injector.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION OF THE INVENTION

Figure 1:
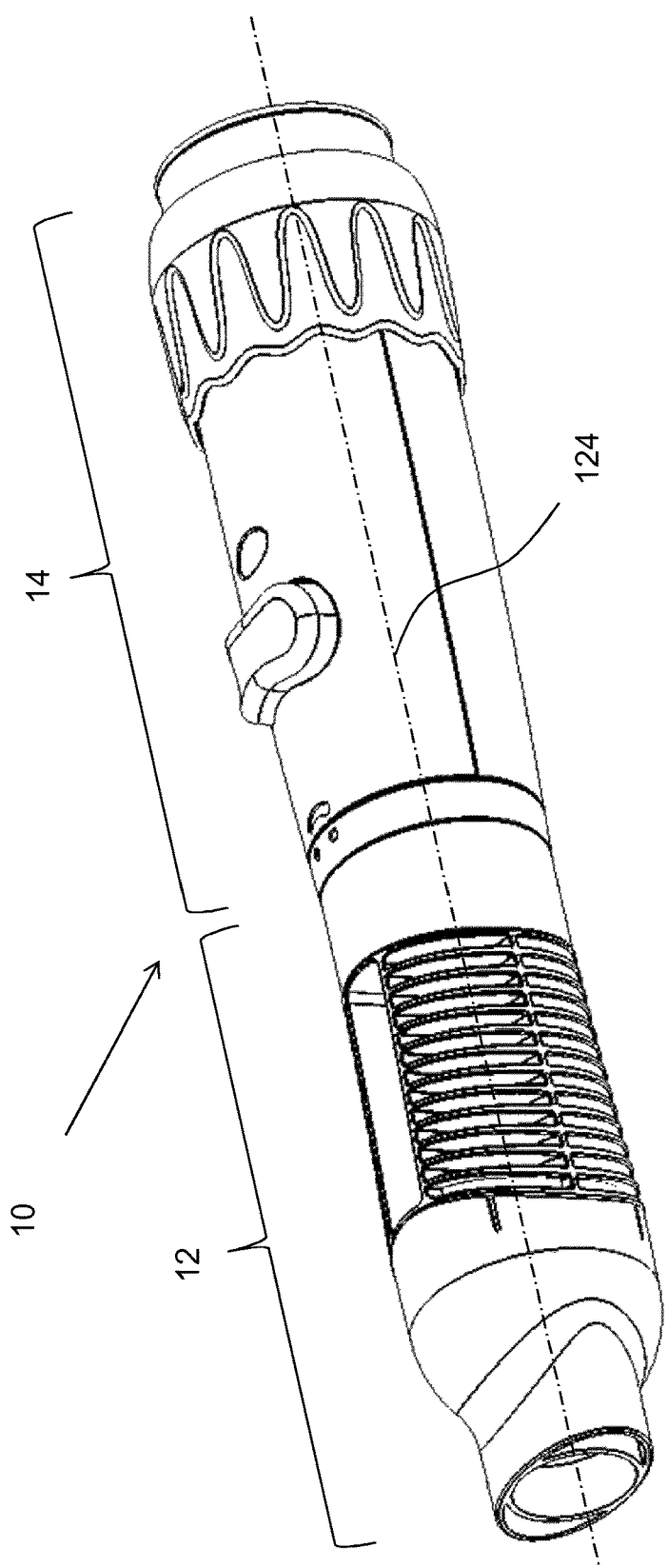
FIG. 1 is a perspective view of a medicament delivery device comprising the present invention.

One embodiment of a device shown in the drawings comprises a generally elongated body 10. The body 10 is in the embodiment shown divided into two parts; a proximal part 12 and a distal part 14, FIG. 1.

Figure 2:
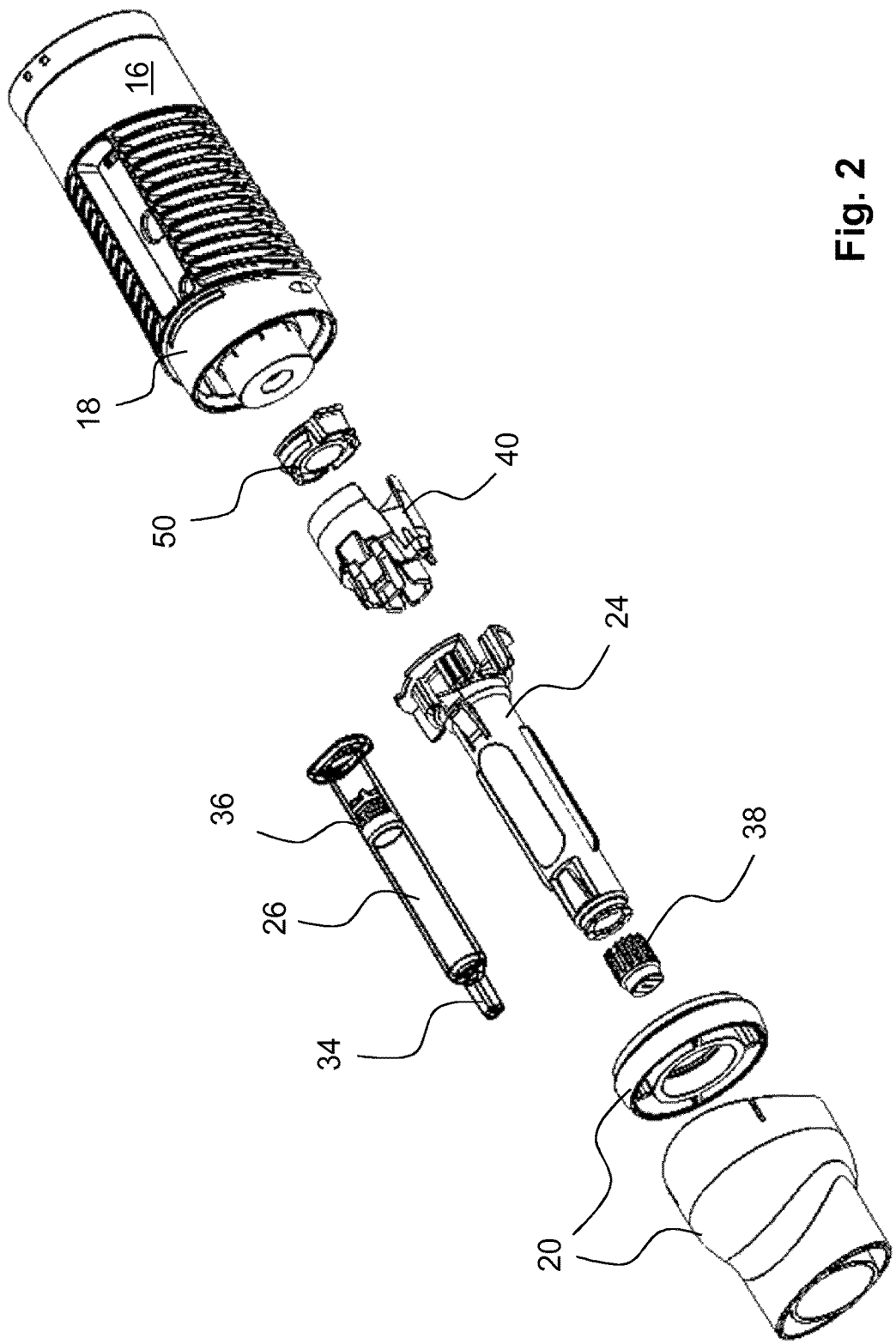
FIG. 2 is an exploded view of a proximal part of the device of FIG. 1.

The proximal part 12 comprises a generally tubular housing part 16, FIG. 2. A proximal end of the housing part 16 is arranged with an attachment area 18, FIG. 2, onto which a medicament delivery member 20 can be releasably attached. The attachment means between the medicament delivery member 20 and the housing 16 could for example be ledges 22 that snap into corresponding grooves 23 (not shown). It is however to be understood that other types of attachment means could be utilized. The medicament delivery member 20 is in the embodiment shown a mouthpiece through which a user inhales when a dose of medicament is to be delivered. It is however to be understood that other types of medicament delivery members could be used, such as nasal pieces, eye pieces and even injection needles and the like.

The proximal part 12 is further arranged with a generally elongated tubular medicament container holder 24, FIG. 2, arranged to accommodate a medicament container 26. The medicament container holder 24 is arranged with generally radially flexing legs 28, FIG. 3, with outwardly extending ledges 30 that fit into recesses 32 in the housing part 16.

The medicament container 26 is in the embodiment shown arranged with a proximal neck 34 and a movable stopper 36 inside the container. At the proximal end of the medicament container holder 24, a nebulizing nozzle 38 is arranged, FIGS. 2 and 3. The nebulizing nozzle 38 contains a chip (not shown) with a plurality of micro channels capable of creating an aerosol of droplets of medicament.

Figure 3:
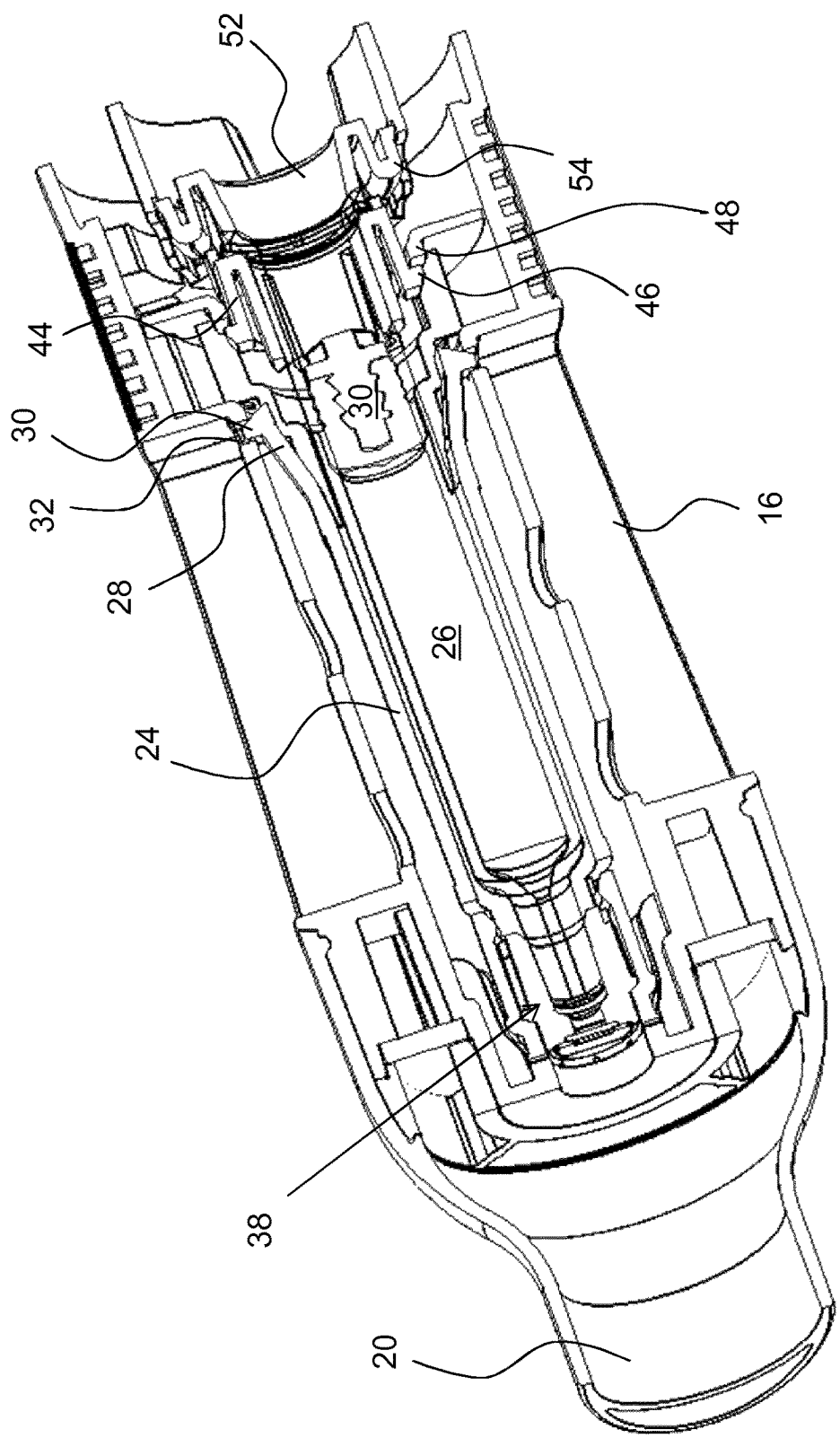
FIG. 3 is a cross-sectional view of the proximal part of FIG. 2
Figure 4:
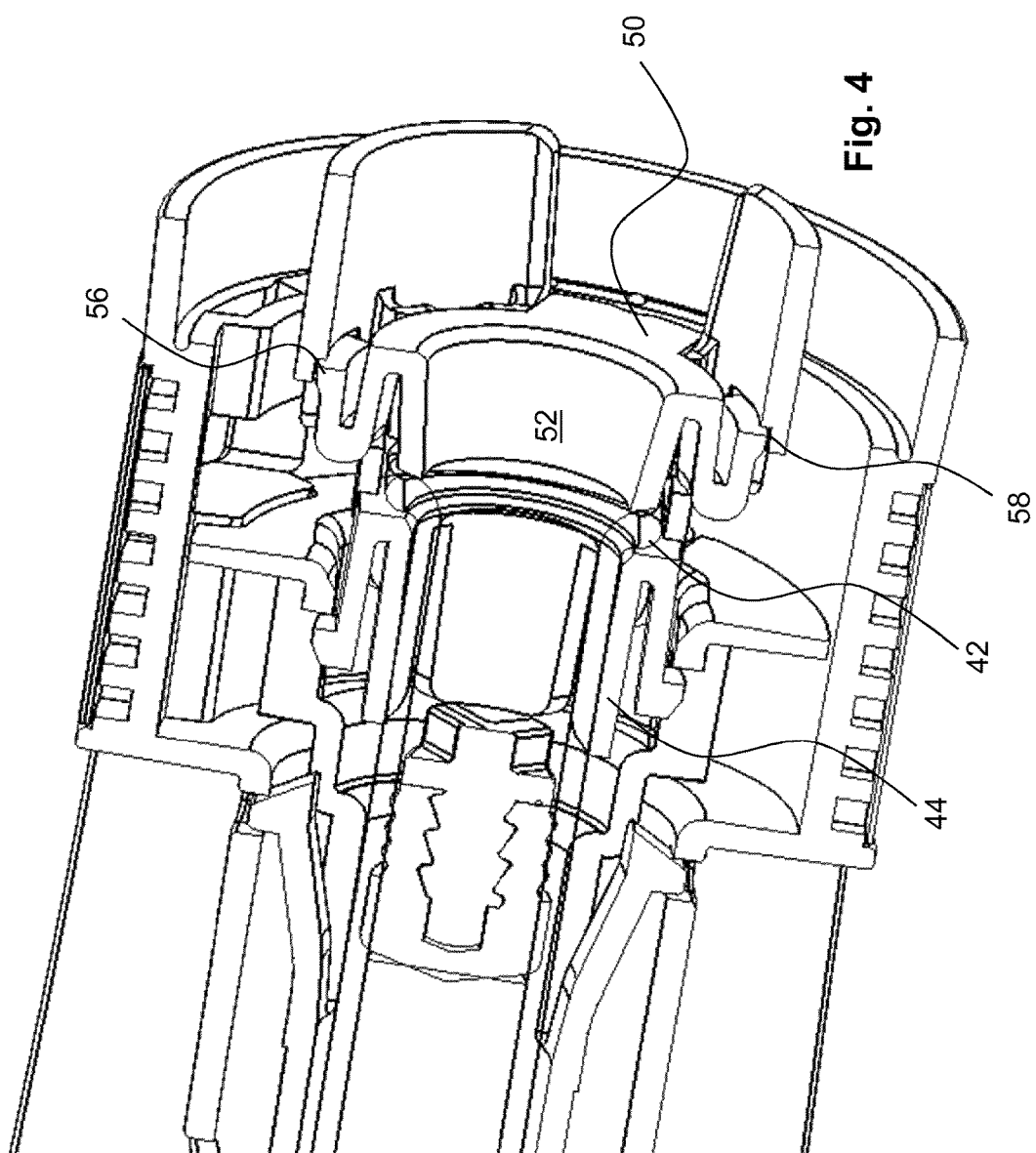
FIG. 4 is a detailed view of a cross-sectional, distal area of the proximal part of 2.

A medicament container guide member 40, FIGS. 2 and 3, is arranged with a central passage and is intended to be pushed onto the medicament container 26 from its proximal end and into contact with an annular ledge 42 at the distal end of the medicament container 26, FIG. 4. The medicament container guide member 40 is arranged with a number of proximally extending arms 44, FIG. 3, arranged generally radially flexible and having outwardly extending protrusions 46. These protrusions 46 are arranged to grip around an annular ledge 48 of the housing for locking the medicament container guide member 40 and thus the medicament container 26 in the radial direction.

A medicament holder locking member 50, FIG. 4, is arranged to be pushed into the distal end of the medicament container holder 24, and moved in contact with a distally directed end surface of the medicament container 24. The medicament holder locking member 50 is arranged with a central passage 52 and is provided with a number of generally radially flexible tongues 54 having outwardly extending protrusions 56, FIG. 4. These protrusions 56 are arranged to fit into recesses 58 on inner surfaces of the medicament container guide member 40 such that when the medicament holder locking member 50 is in place, the medicament container 26 is locked in the axial direction.

The distal part 14 is arranged with a housing. In the embodiment shown the housing is designed as two housing halves 60, 62, FIG. 6. It is however to be understood that the housing may be arranged in other ways and in more parts without departing from the scope of the invention.

Figure 5:
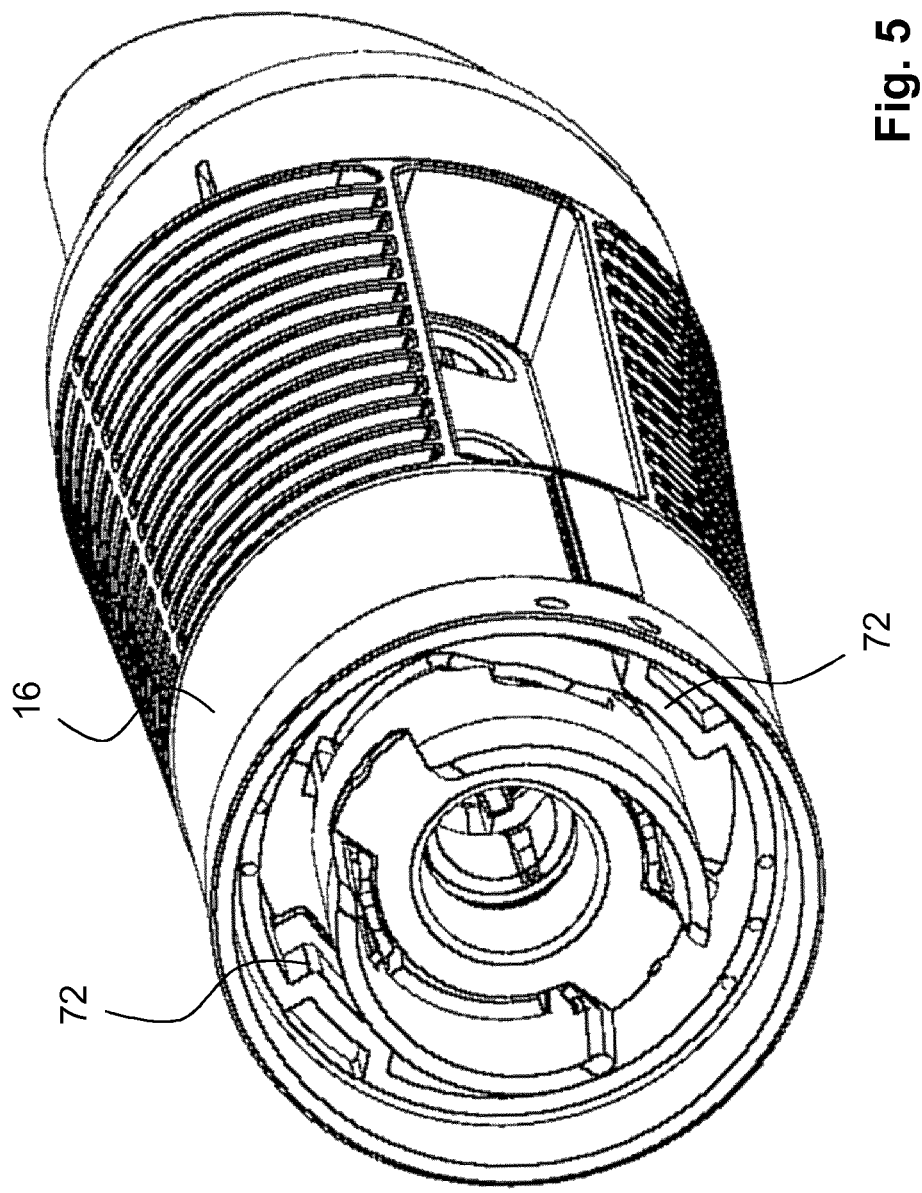
FIG. 5 is a perspective view of a distal area of the proximal part of FIG. 2.
Figure 6:
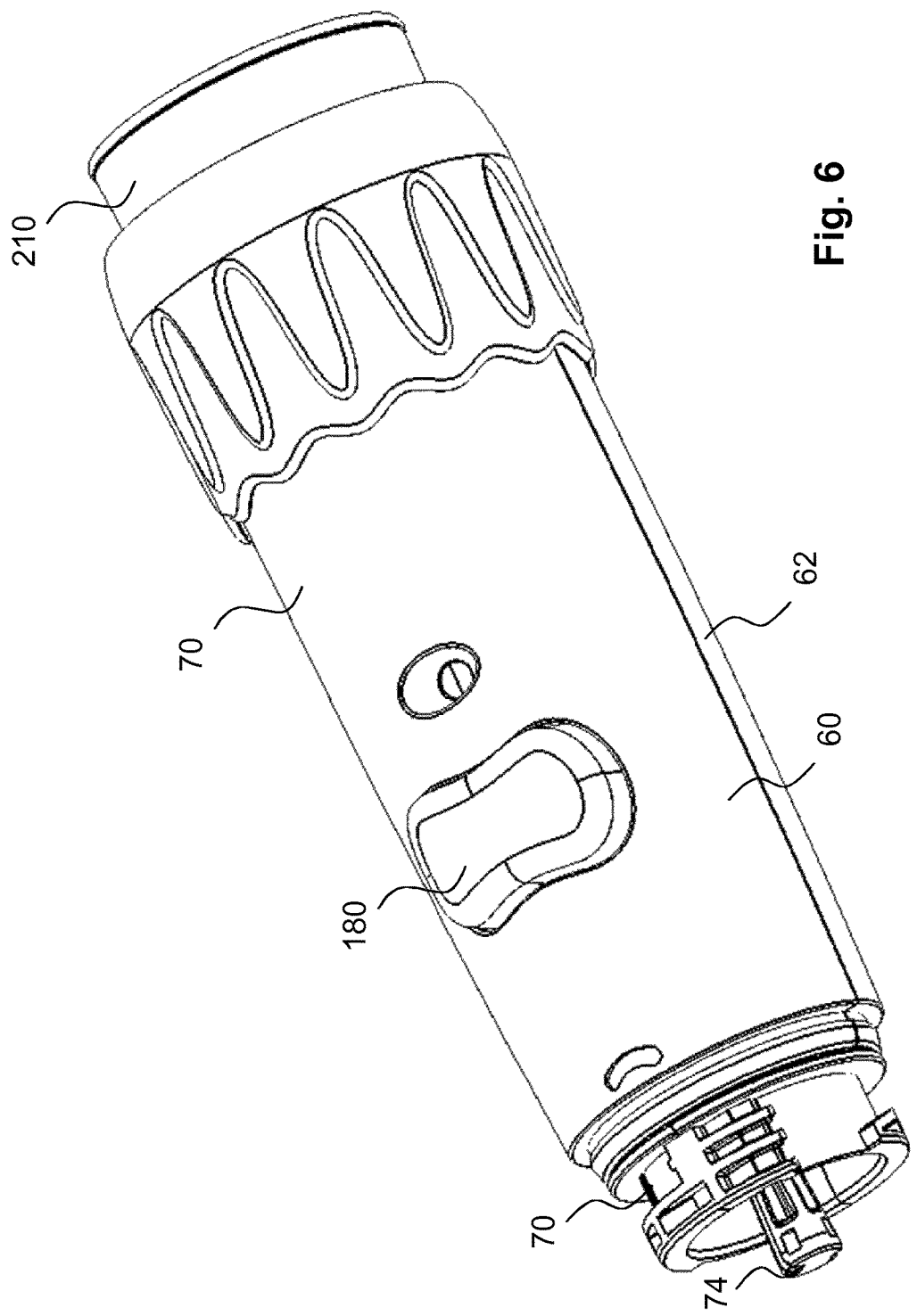
FIG. 6 is a perspective view of a distal part of the device of FIG. 1.
Figure 7:
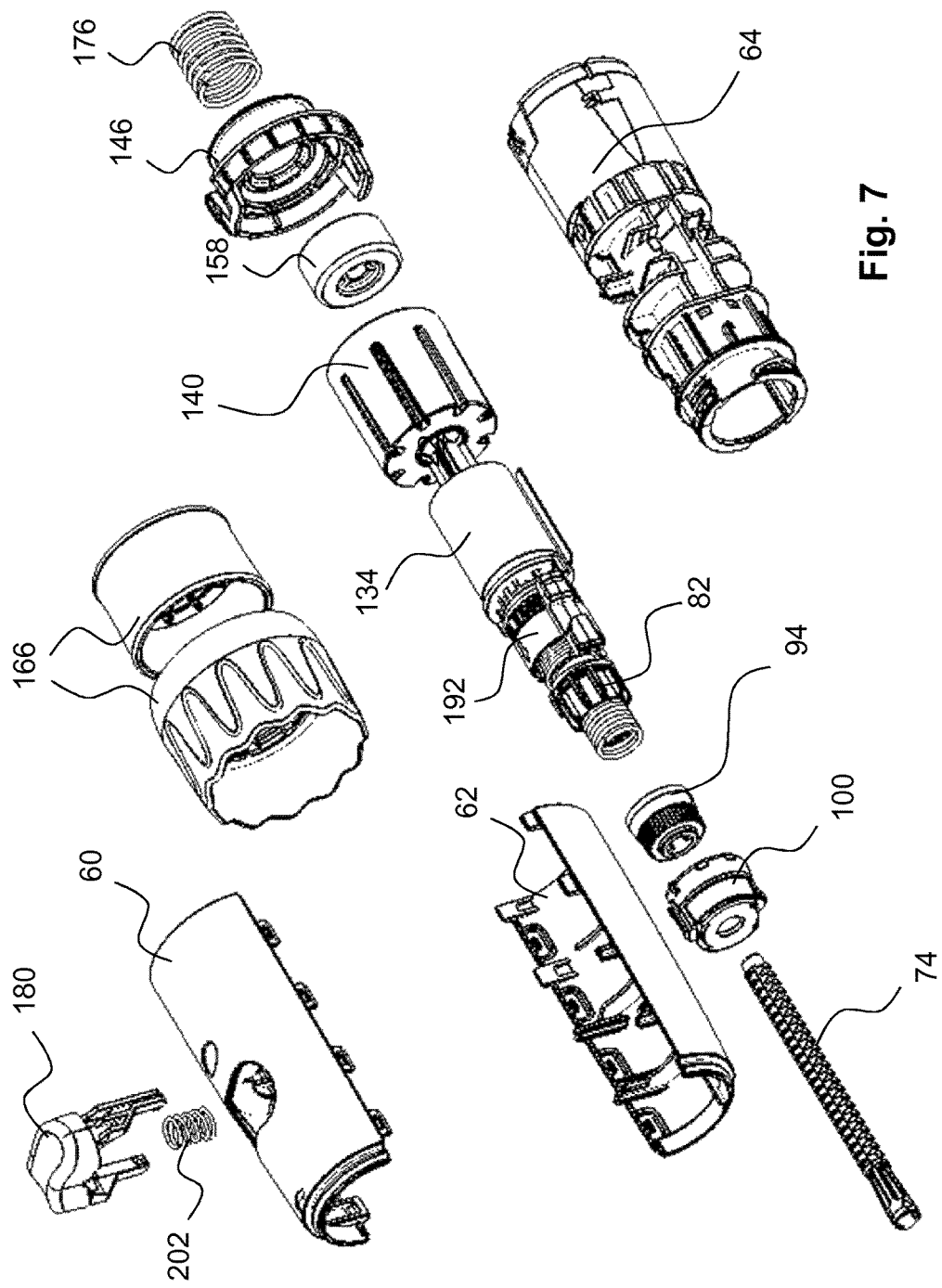
FIG. 7 is an exploded view of the distal part of FIG. 6.

Inside the distal part, a generally tubular chassis 64 is arranged, FIGS. 7, 9, 10. It is arranged with a transversal interior wall 66, FIGS. 9 and 10. The interior wall 66 is further provided with a central passage 68. At a proximal end of the chassis, attachment means 70, FIG. 6, are arranged, in the embodiment shown as grooves for a bayonet connection. In this context it is to be understood that other types of attachment means may be employed, such as threads, snap-on fittings or the like, all within the imagination of the person skilled in the art. The attachment means 70 of the chassis 64 are intended to interact with corresponding attachment means 72 on the distal end of the generally tubular housing part 16, FIG. 5.

Coaxially arranged inside the chassis 64 and extending in the longitudinal direction of the device is an elongated plunger rod 74, FIGS. 6 and 7. The plunger rod 74 is intended to be in contact with a stopper arranged in the medicament container. The plunger rod 74 is arranged inside a so called drive member extension 76, FIGS. 11 and 12, having a generally tubular shape. A proximal end of the drive member extension 76 is arranged with spline grooves 78 on its outer surface, FIGS. 11 and 12. The spline grooves 78 mate with corresponding spline ridges 80 on an inner surface of a generally tubularly shaped drive nut 82, FIG. 11.

Figure 11:
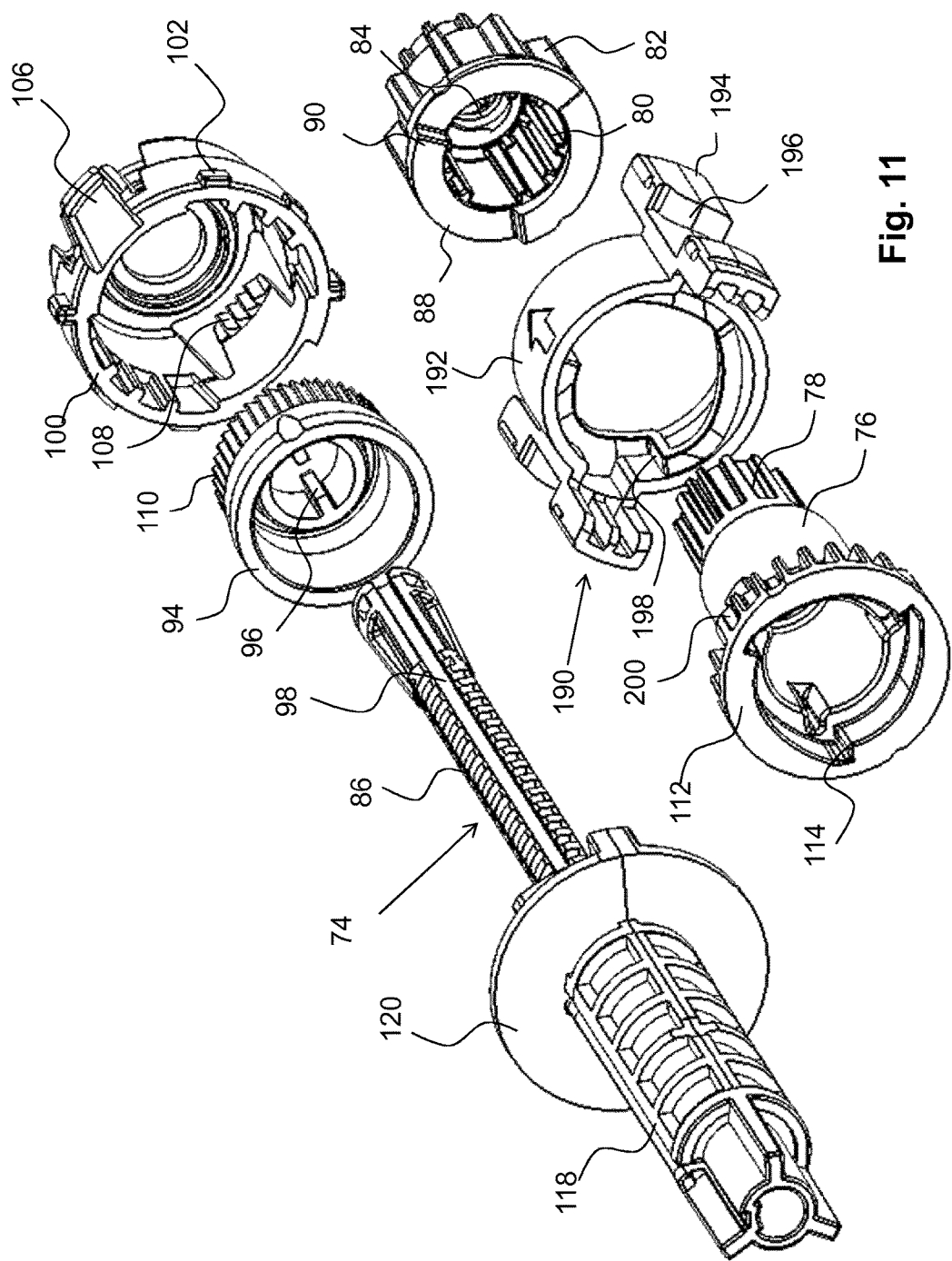

The inner surface of the drive nut 82, FIG. 11, is further provided with threads 84, which cooperate with threads 86 on the outer surface of the plunger rod 74. The drive nut 82 is further arranged with an annular ledge 88 with a distally directed end surface having a number of slanting wedge-shaped surfaces 90. The proximally directed surface of the interior wall 66 of the chassis 64 is arranged with corresponding slanting wedge-shaped surfaces 92, FIG. 9.

Figure 8:
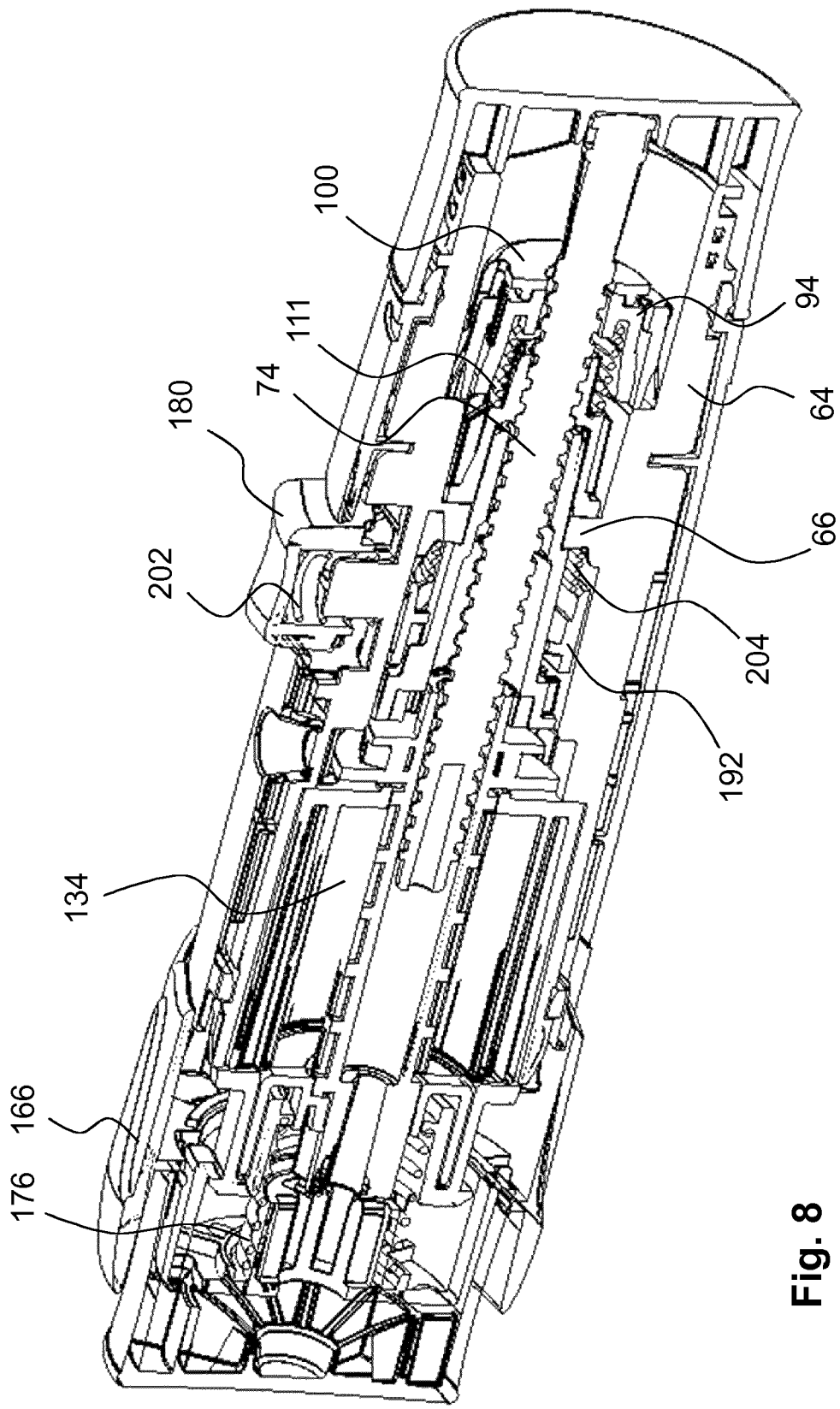
FIG. 8 is a cross-sectional view of the distal part of FIG. 6, FIGS. 9-18 are detailed views of components comprised in the distal part of FIG. 6, FIGS. 19-20 are detailed views showing different functional states.

The plunger rod 74 is further arranged through a guide nut 94, FIG. 11. The guide nut 94 is arranged with guide ledges 96 which cooperate with longitudinal grooves 98 of the plunger rod 74, FIG. 6, providing a rotational lock but allowing a longitudinal movement of the plunger rod 74 in relation to the guide nut 94. The guide nut 94 fits into a guide nut lock member 100, which is attached to the chassis 64 via radially outwardly extending protrusions 102 fitting into recesses 104 in the interior surface of the chassis 64, FIG. 9. The nut lock member 100 is arranged with tongues 106 that are arranged flexible in the generally radial direction. The inner surfaces of the flexible tongues 106 are arranged with wedge-shaped teeth 108, FIG. 11, extending in the radial direction. The teeth 108 of the tongues 106 are intended to engage corresponding wedge-shaped teeth 110 arranged around the circumference of the guide nut 94. A spring 111, FIG. 8, is arranged between the drive nut 82 and the guide nut 94 for urging the latter in the proximal direction.

Further, the drive member extension 76 is arranged with a ring-shaped part 112, FIG. 11, with a hollow interior, where the inner surface of the interior is arranged with transversal stop ledges 114. These stop ledges 114 cooperate with flexible arms 116 arranged at a proximal end of a generally elongated drive member 118, FIG. 12.

However the stop ledges 114 and flexible arms 116 are arranged such that the drive member 118 may only be rotated in one direction in relation to the drive member extension, where the flexible arms 116 slide over the stop ledges 114. In the other direction, the ends of the flexible arms 116 abut the stop ledges 114, thereby blocking their relative rotation. The drive member 118 is further arranged with a disk-shaped member 120, FIG. 12. On the proximally directed side of the disk-shaped member 120, two stop ledges 122 are arranged diametrically on opposite sides of a longitudinal axis 124, FIG. 1, of the device. The stop ledges 122 are arranged to co-act with corresponding stop ledges 126, FIG. 10, arranged in the interior of the chassis 64 for limiting the rotation of the drive member 118.

Figure 12:
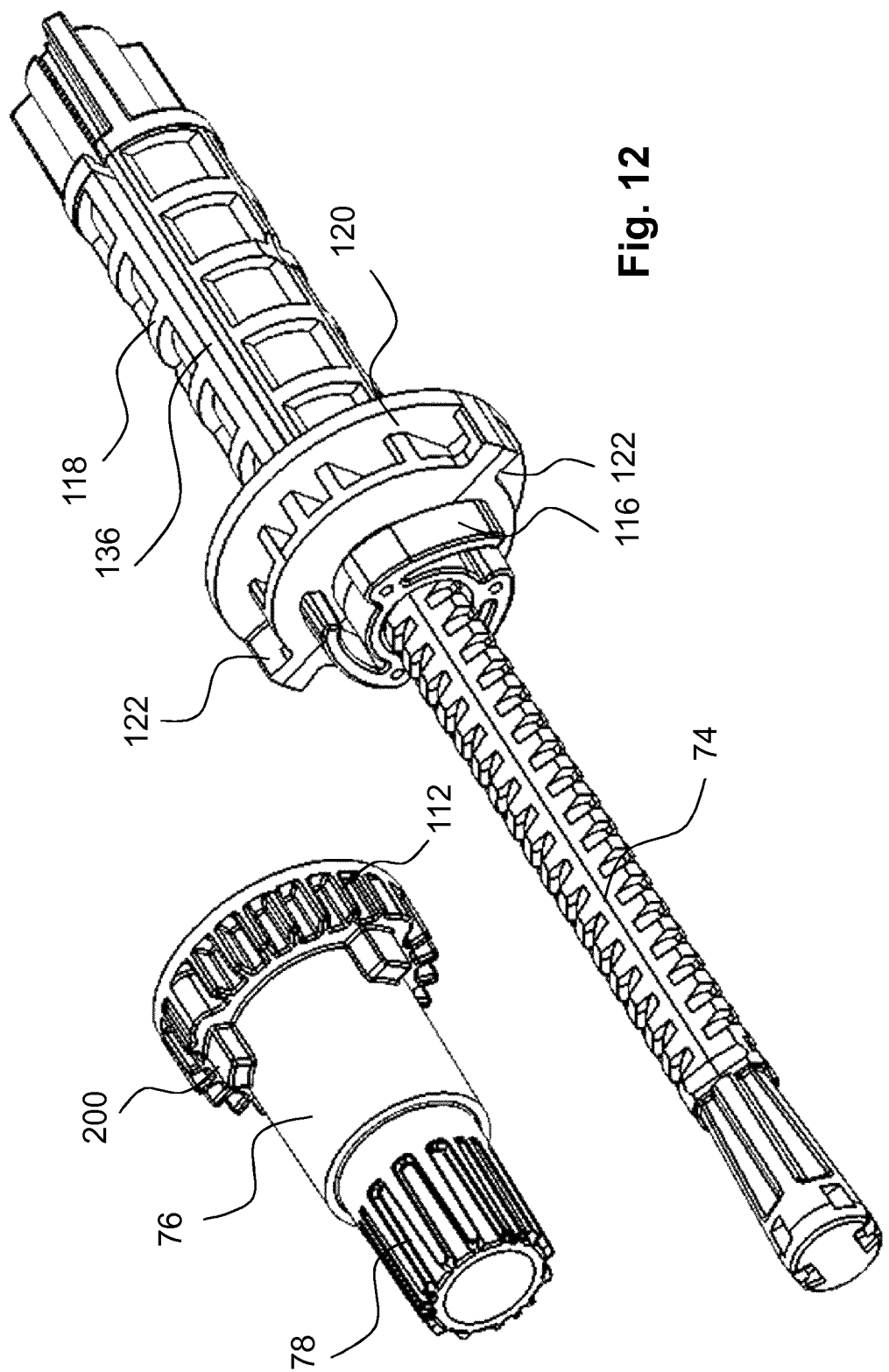
Figure 13:
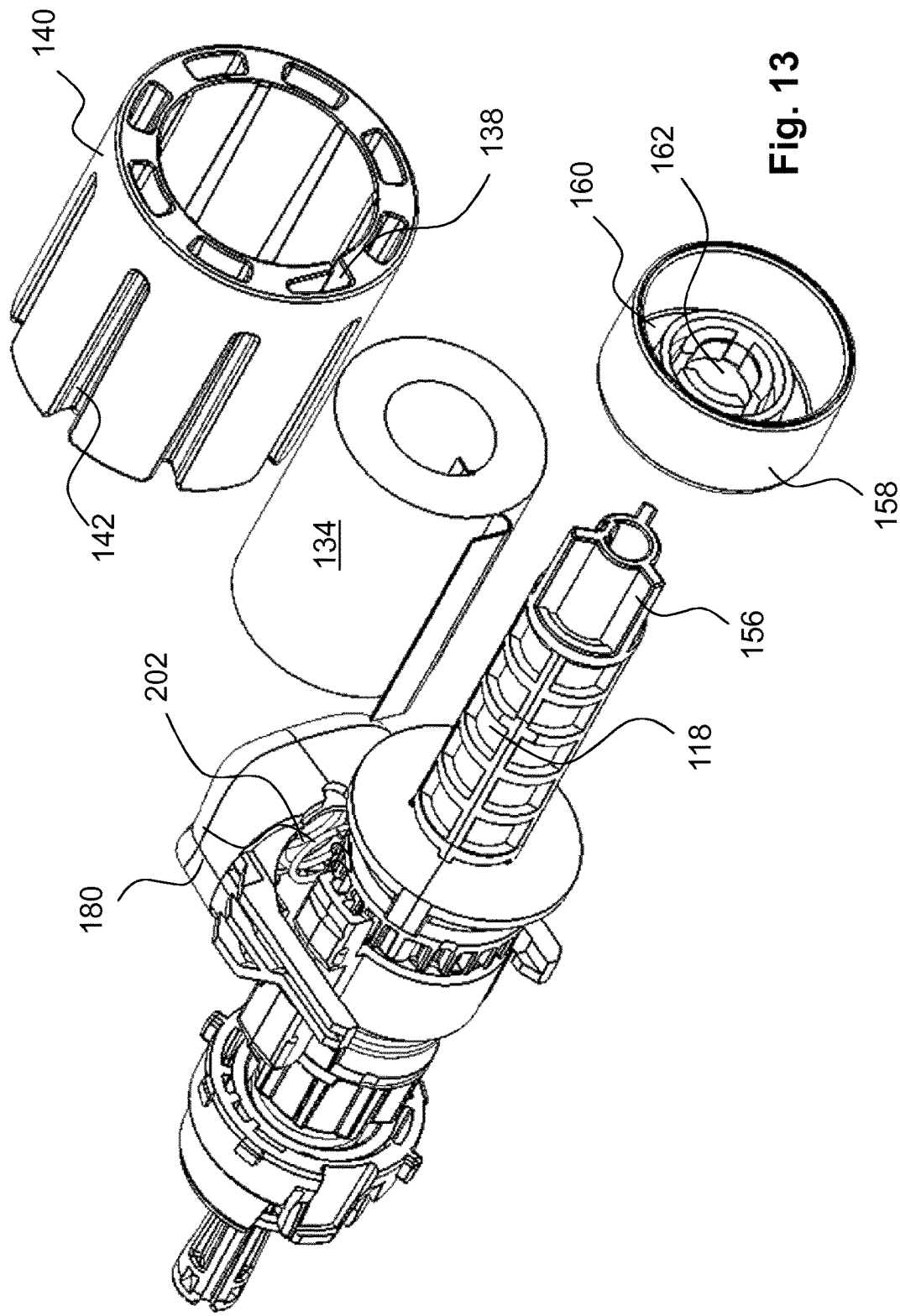
Figure 14:
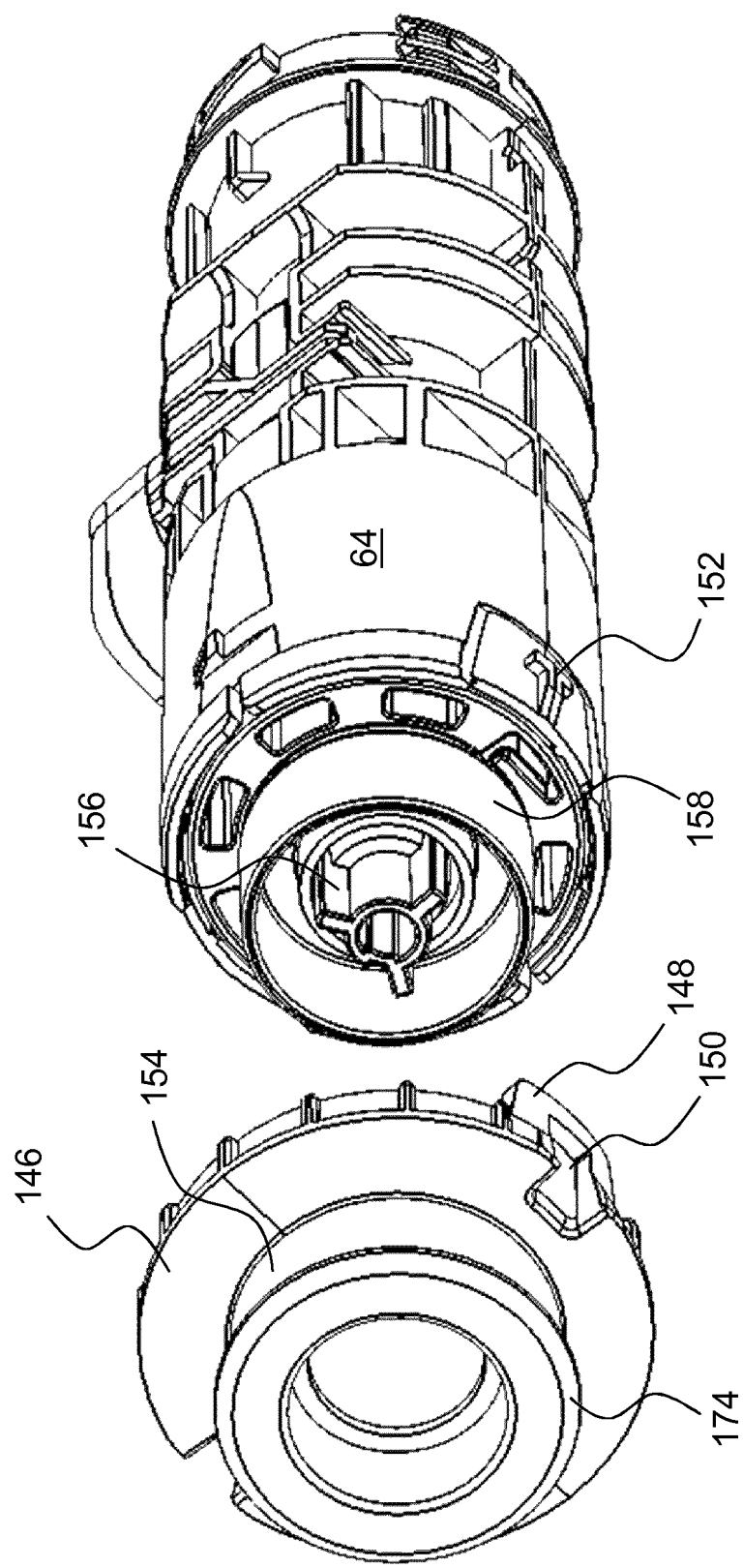

A spring force member, shown as a spiral drive spring 134, FIG. 13, is arranged around the drive member 118 and attached with an inner end in an elongated slit 136, FIG. 12, in the drive member 118 and with the other end in a slit 138 in a spring house 140, FIG. 13. The spring house 140 is in turn placed inside the distal part of the chassis 64, FIG. 10, and held fixed in relation to the chassis 64 by longitudinal grooves 142 in the outer surface of the spring house 140 fitting with corresponding ridges 144. The spring house 140 is held in place in the chassis 64 by a spring house cover 146, FIG. 14, which is attached to the chassis 64 by proximally directed arms 148 with passages 150, which accommodate ledges 152 on the outer surface of the chassis 64. The spring house cover 146 is further arranged with a distally directed tubular member 154.

Figure 15:
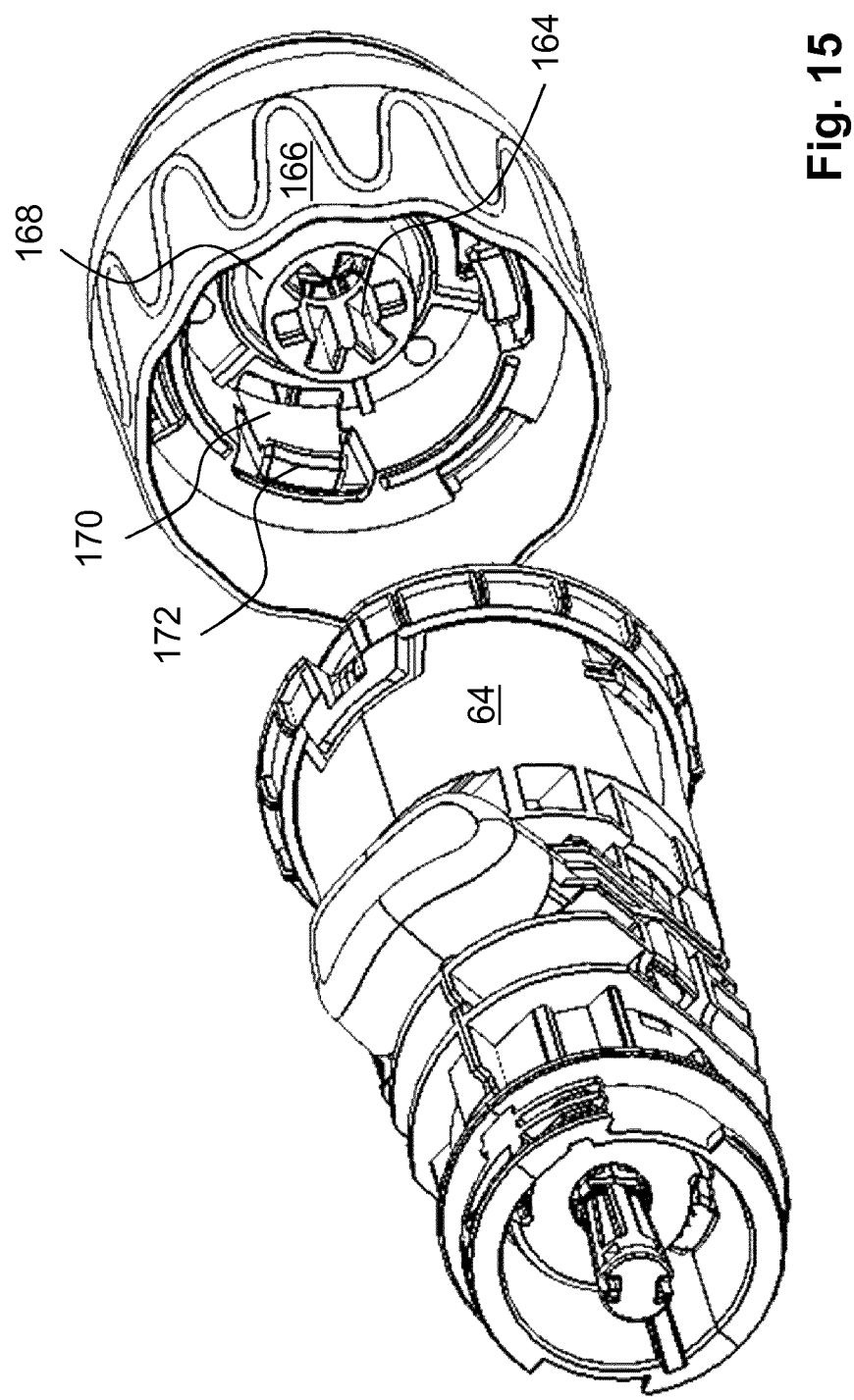
Figure 18:
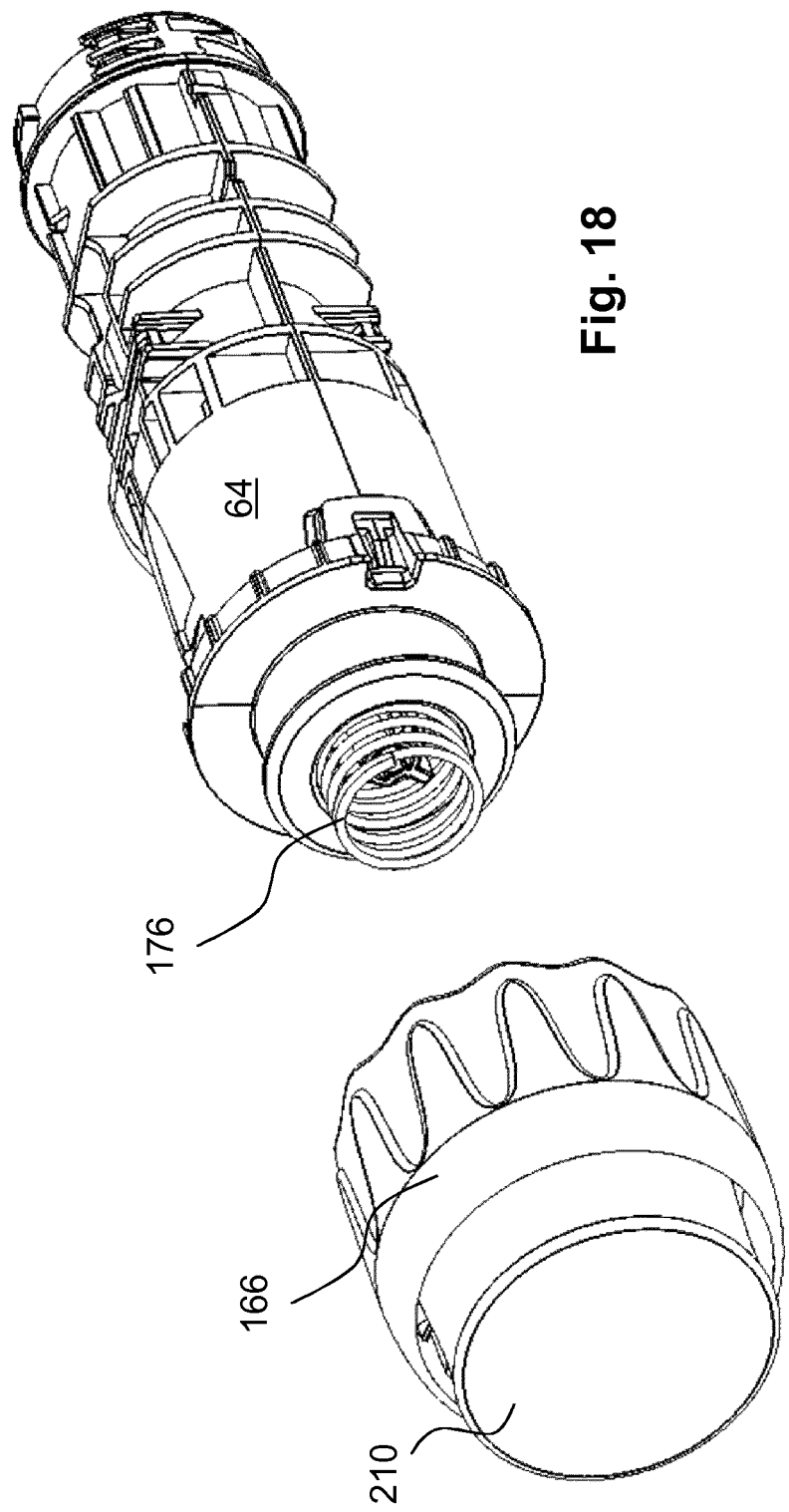

The distal end of the drive member 64 with the ledges 156 are further arranged to fit into a corresponding recess 164 on a dose knob 166, FIG. 15. The recess 164 is positioned on a central post 168 inside the dose knob 166, FIG. 15. The dose knob 166 is further arranged with a number of proximally directed arms 170, which arms 170 are flexible in the generally radial direction. The free ends of the arms 170 are arranged with inwardly extending ledges 172, which ledges 172 are designed to fit around an annular ledge 174, FIG. 14, arranged on the circumference of the tubular member 154. A spring 176, FIG. 18, is further arranged between an end wall 160 of a guide member 158 (not shown) and an interior, proximally directed wall of the dose knob 166, urging the latter in the distal direction.

Figure 16:
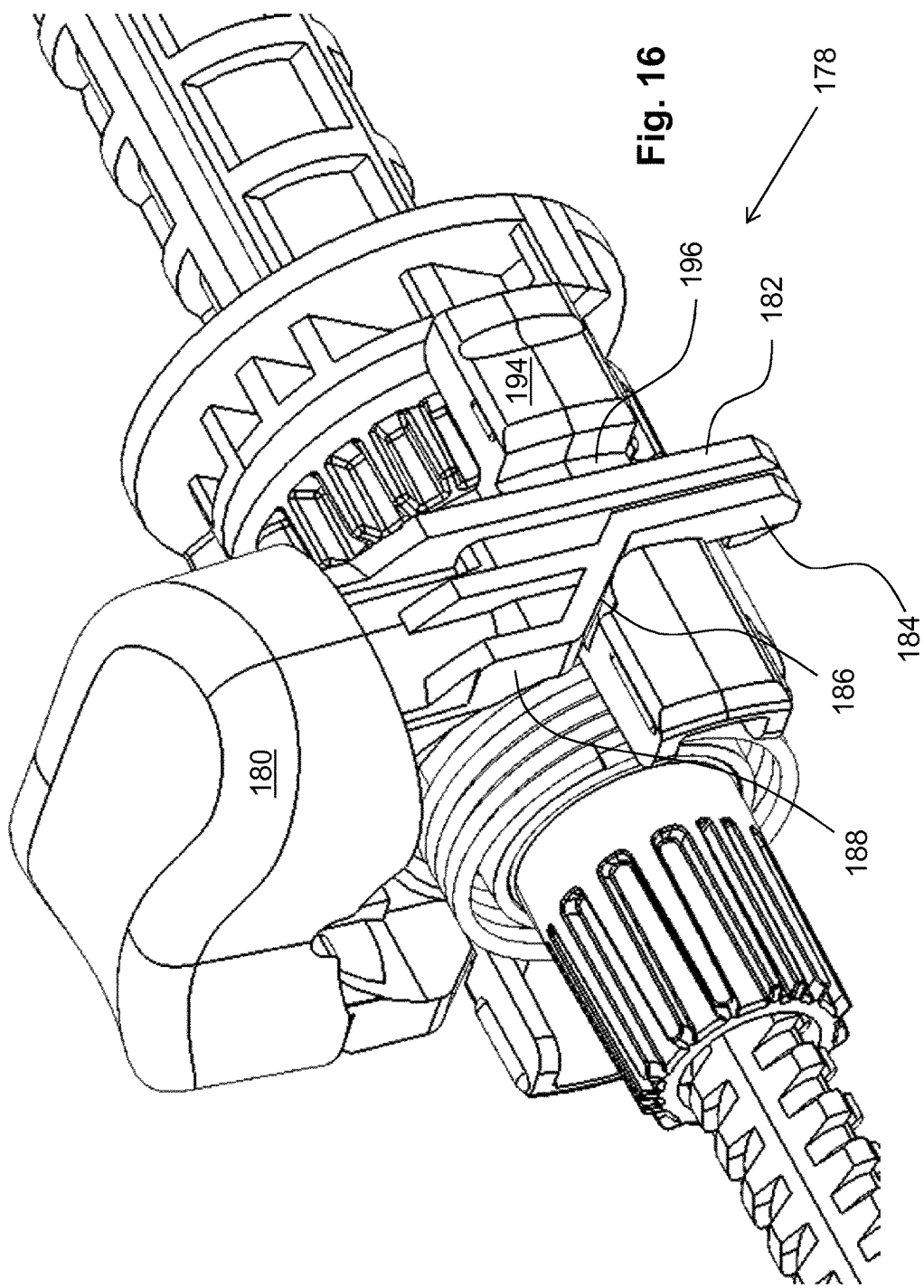

Further, an activation mechanism 178, FIG. 16, is arranged in the device. It comprises an activation button 180 extending through an opening of one of the housing halves 60. The activation button 180 comprises two inwardly extending arms, 182, one on each side of the longitudinal direction 124 of the device. Each arm 182 is arranged with a first surface 184 facing in the proximal direction. The first surface 184 transitions into a second surface 186, inclined with respect to the first surface 184. The second surface 186 thereafter transitions into a third surface 188 generally parallel with the first surface 184.

Figure 17:
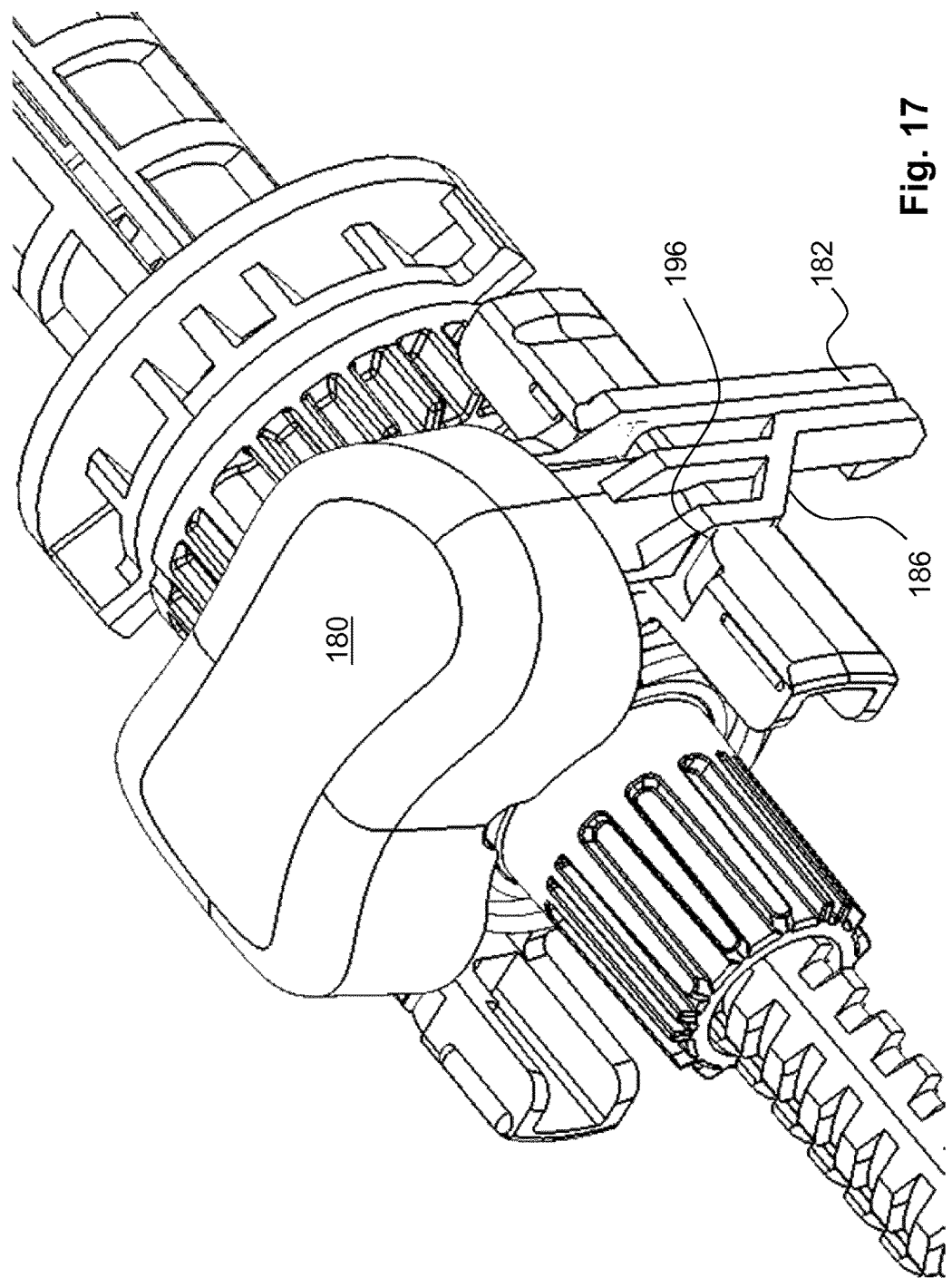

The arms 182 are in contact with a dose activator 190, FIG. 11, comprising a ring-shaped body 192, FIG. 11, surrounding a part of the drive member extension 76. The ring-shaped body 192 is arranged with two elongated posts 194, extending in the longitudinal direction of the device. Each post is arranged with a groove 196, in which grooves the arms 182 of the activation button 180 fit, FIG. 17.

A distally directed end surface of the ring-shaped body 192 is arranged with an engagement mechanism comprising a number of circumferentially directed stop ledges 198, FIG. 11, the function of which will be described below. The stop ledges 198 are to interact with stop ledges 200 on an outer surface of the drive member extension 76. A compression spring 202, FIG. 13, is arranged between an interior surface of the activation button 180 and an outer side surface of the chassis 64 for urging the activation button 180 towards an extended position. Further a second compression spring 204, FIG. 8, is arranged between a proximally directed end surface of the ring-shaped body 192 of the dose activator 190 and a distally directed surface of the transversal wall 66 for urging the ring-shaped body 192 in the distal direction and in engagement between the stop ledges 198 of the ring-shaped body 192 and the stop ledges 200 of the drive member extension 76.

Figure 19:
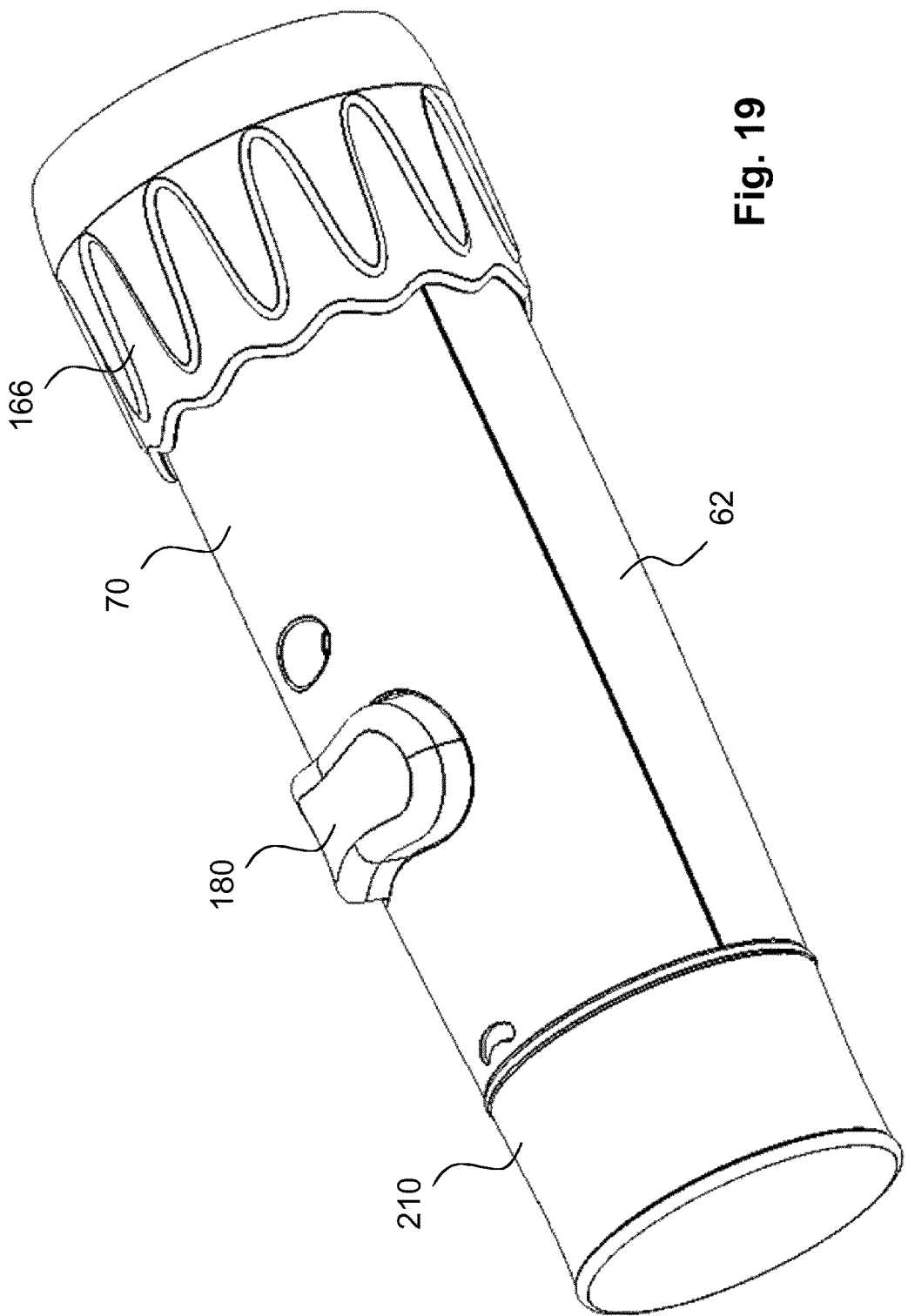
FIG. 19 is a perspective view of the distal part of the device of FIG. 1 arranged with a plunger rod positioning member according to the invention.
Figure 20:
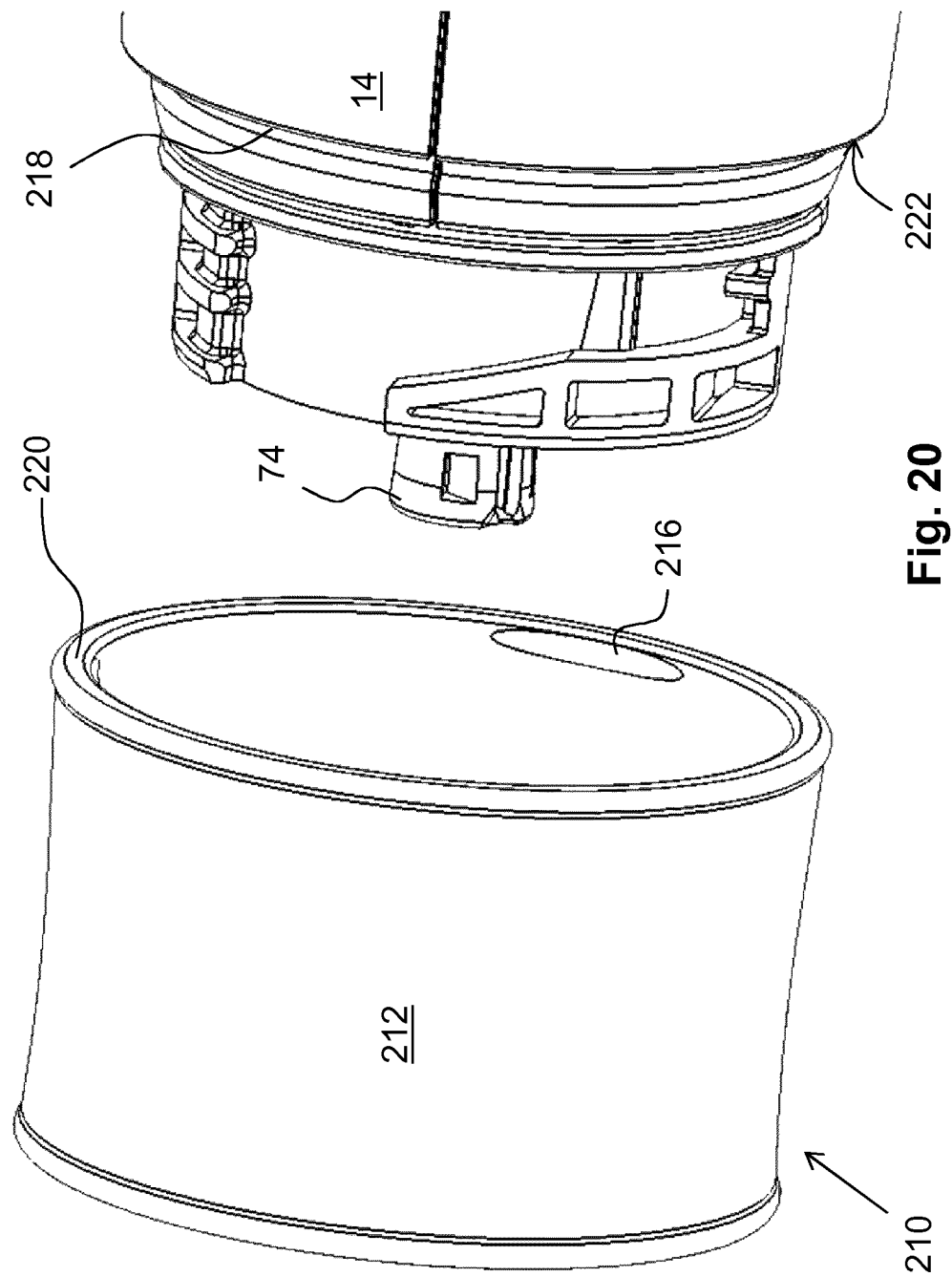
FIG. 20 is a detailed view of the plunger rod positioning member according to FIG. 21.
Figure 21:
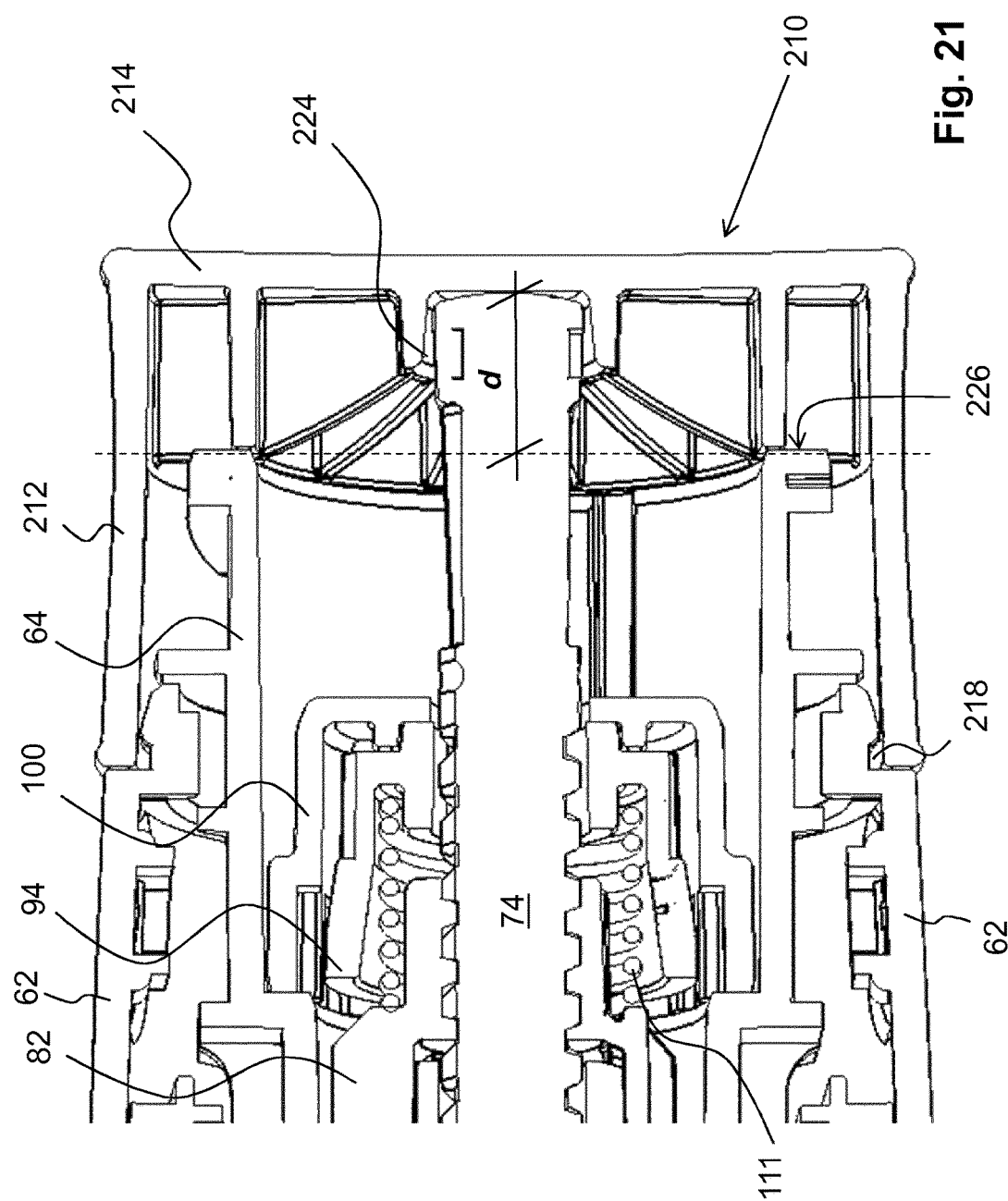
FIG. 21 is a cross-sectional detailed view of the plunger rod positioning member according to FIG. 21.

The present invention is further arranged with a plunger rod positioning member 210, e.g. a cap, FIGS. 19 to 21. In the embodiment shown the plunger rod positioning member is arranged as a generally tubular body 212 that together with an end wall 214, forms a cap, FIG. 21. On the inner surface of the tubular body adjacent an edge 220, first holding members, in the form of inwardly directed ledge portions 216, FIG. 20, are arranged. The ledge portions 216 are arranged to cooperate with second holding members, in the form of an annular groove 218, arranged at the proximal end of the distal part 14 when a distally directed end surface 220 of the cap is moved in contact with a proximally directed annular ledge 222 of the distal part. An interior surface of the end wall 214 of the cap may further be arranged with a centrally positioned seat 224, FIG. 21, in which the plunger rod 74 may fit.

The device is intended to function as follows. When the device is delivered to a user for the first time, the proximal and the distal parts are delivered separate from each other. Also the medicament container may be delivered separate from the proximal part. The distal part 14, when delivered, has the cap attached to its proximal end, FIG. 19. When the plunger rod positioning member 210 has been attached to the device during assembly before delivery to a user, the plunger rod positioning member 210 is used to position the plunger rod 74 at a certain predetermined distance d in relation to a proximal end surface 226 of the distal part 14, FIG. 21. Thus the proximal end of the plunger rod 74 is fitted into the seat 224 of the cap 210, FIG. 23. In this way the cap also protects the device, and especially the plunger rod during handling, i.e. before the proximal and the distal parts are assembled. When no proximal part is attached to the distal part, the teeth 108 of the tongues 106 of the guide nut lock member 100 are out of engagement with the teeth 110 of the guide nut 94. The guide nut 94 is thus free to rotate, and when the plunger rod 74 is pushed in the distal direction by the plunger rod positioning member 210, it may rotate together with the guide nut 94, in relation to the chassis 64 and the drive nut 82, thereby moving the plunger rod 74 in the distal direction of the device.

The plunger rod 74 is moved in the distal direction until the edge 220 of the plunger rod positioning member 210 is moved in contact with the annular ledge 222 of the distal part, when the ledge portions 216, fit into the annular groove 218 of the distal part 14. The dimensions of the cap in relation to the annular ledge 222 and the distance to the proximal end 226 of the device are chosen such that the plunger rod protrudes a certain pre-determined distance d beyond the proximal end of the device. When the device made ready for use, the plunger rod positioning member 210 is removed. It may then be attached to a distal end of the device for later re-use as seen in FIG. 6 and FIG. 18. When plunger rod positioning member cap is removed, the plunger rod protrudes that pre-determined distance d beyond the proximal end surface 226 of the distal part 14.

Now the proximal part 12 is connected to the proximal end of the distal part 14. First, an appropriate medicament container 26 is placed in the medicament container holder 24 together with the medicament container guide member 40 such that its arms snap in engagement with the medicament holder. The medicament holder is subsequently inserted into the housing part 16. Then the medicament holder locking member 50 is pushed in engagement with the medicament container guide member 40. The proximal part 12 is thereafter connected to the distal part 14 and the chassis 64 via the attachment means 70, 72.

During connection, the proximal end of the plunger rod is moved into contact with the stopper of the medicament container. Thus, the pre-determined distance, d, of the protruding plunger rod has been chosen such that it is ascertained that there is a positive contact between the proximal end of the plunger rod and the stopper, regardless of any differences in tolerances of the medicament container and regardless of any differences in actual position of the stopper inside a full medicament container. Thereby it is ascertained that the initial dose from the device really is a full dose of medicament. Otherwise, if there is a gap between the plunger rod and the stopper at the initial dose delivery, the first delivered dose will not be a full dose.

The distal end of the medicament container guide member 40 is designed such that it engages the outer surface of the guide nut lock member 100, whereby the tongues 106 are pressed radially inwards such that the teeth 108 of the tongues 106 engage the teeth 110 of the guide nut 94, whereby the guide nut 94 becomes rotationally locked.

When a dose is to be set and delivered the dose knob 166 cooperates with the drive member 118 in spring force tensioning mechanism, when operated, e.g. rotated. In order to connect the dose knob 166 to the dose setting mechanism, the dose knob 166 is pushed in the proximal direction against the force of the spring 176. The dose knob 166 and the drive member 118 are then connected in that the ledges 156 fit into the recess 164. Thus, when the dose knob 166 is rotated, the drive member 118 is also rotated. The rotation of the drive member 118 causes the spiral drive spring 134 to be tensioned from an initial state where it was pre-tensioned during manufacture of the device.

During rotation, the flexible arms 116 of the drive member 118 move out of contact with the stop ledges 114 of the ring-shaped member 112 of the drive member extension 64 until they are moved in contact with subsequent stop ledges 114. The drive member 118 is prevented from being rotated back because the contact of the flexible arms 116 with the stop ledges 114.

Further, the drive member extension 64 is in turn prevented from rotating because the stop ledges 198 of the dose activator 192 are in contact with the stop ledges 200 on the drive member extension 64.

The dose knob 166 is rotated until the stop ledge 122 of the drive member 118 comes in contact with the corresponding stop ledge 126 of the chassis 64. This ensures that the user cannot turn the dose knob 166 beyond a pre-set position. Therefore a too large dose cannot be set.

The user may now position the medicament delivery device at the delivery site and may manually activate the medicament delivery device by pressing the activation button 180 into the device against the force of the return spring 202. The movement of the activation button 180 causes the arms 182 to slide in the grooves 196 of the posts 194. After a certain movement, the inclined second surface 186 is moved in contact with a distally directed surface of the groove 196 and thereafter the third surface 188, FIG. 17. This contact of the second and third surfaces forces the ring-shaped body 192 in the proximal direction. This in turn causes the stop ledges 198 of the dose activator 190 to move out of contact with the stop ledges 200 of the drive member extension 64. The drive member extension 64 and thereby the drive member 118, because of the connection between the flexible arms 116 and the stop ledges 114, are now free to rotate by the force of the spring 134, and due to the splines connection between the drive member extension 64 and the drive nut 82, the latter is also rotated.

Due to the rotation of the drive nut 82, which is in threaded engagement with the threads 86 of the plunger rod 74, and because of the rotational lock of the plunger rod with the guide nut 94, the plunger rod 74 is axially advanced, which causes it to move the stopper 36 inside the medicament container 26 and to force the medicament through the medicament delivery member, e.g. the nebulizing nozzle 38 and the mouth-piece 20.

It is to be understood that the embodiment described above and shown in the drawings is to be regarded only as a non-limiting example of the invention and that it may be modified in many ways within the scope of the patent claims.

The invention claimed is:

1. A metered droplet medicament delivery device, comprising:
    a proximal part and a distal part having opposite distal and proximal ends, the proximal part and the distal part being releasably connectable to each other;
    a medicament container with a movable stopper;
    a dose delivery mechanism, comprising a plunger rod operably arranged to act on the stopper; and
    a plunger rod positioning cap configured to engage a proximal end of the plunger rod and to engage a proximal area of the distal part for positioning the plunger rod in a longitudinal position of the device relative to the proximal area;
    wherein the proximal part comprises a medicament container holder for accommodating the medicament container, the distal part comprises the dose delivery mechanism with the plunger rod, the plunger rod positioning cap is removable from the proximal area of the distal part and is configured to protect the plunger rod when the proximal and distal parts are not connected to each other, and the plunger rod positioning cap is configured to be removed from the proximal area of the distal part by a user of the metered droplet medicament delivery device and then attached to an attachment area of the metered droplet medicament delivery device when the plunger rod positioning cap is disengaged from the proximal area of the distal part, and
    wherein the metered droplet medicament delivery device cannot dispense medicament from the medicament container when the plunger rod positioning cap is attached to the proximal area of the distal part.

2. The metered droplet medicament delivery device of claim 1, wherein the plunger rod positioning cap comprises a seat for the proximal end of the plunger rod, and a contact surface for contacting the distal part.

3. The metered droplet medicament delivery device of claim 1, further comprising first holding members on the plunger rod positioning cap that cooperate with corresponding second holding members on the distal part for releasably holding the plunger rod positioning cap.

4. The metered droplet medicament delivery device of claim 1, wherein the proximal part comprises a plunger rod guide nut lock member configured to rotationally lock a plunger rod guide nut when the proximal part and the distal part are connected to each other.

5. The metered droplet medicament delivery device of claim 1, wherein the dose delivery mechanism further comprises a plunger rod guide nut rotationally locked relative to the plunger rod, and a drive nut threadedly connected to the plunger rod that is rotatable in the distal part such that the plunger rod is rotatable and thereby is movable in a distal direction when in engagement with the plunger rod positioning cap.

6. The metered droplet medicament delivery device of claim 5, wherein the dose delivery mechanism further comprises:
    a rotatable drive member drivingly connected to the drive nut;
    a spring force member having a first end connected to the drive member and a second end connected to a fixed point on a chassis;
    a spring force tensioning mechanism operably connected to the spring force member to tension the spring force member before dose delivery; and
    an activation mechanism releasably interconnected to the drive member by an engagement mechanism for rotationally locking the drive member when the spring force member is tensioned, wherein operation of the activation mechanism releases the drive member and the spring force member, whereby the drive member drives the dose delivery mechanism for delivery of a dose of medicament.

7. The metered droplet medicament delivery device of claim 1, wherein the plunger rod positioning cap is configured for removal from the distal part after positioning of the plunger rod.

8. The metered droplet medicament delivery device of claim 7, further comprising first holding members on the plunger rod positioning cap that cooperate with corresponding second holding members on the distal part for releasably holding the plunger rod positioning cap.

9. The metered droplet medicament delivery device of claim 7, wherein the proximal part comprises a plunger rod guide nut lock member configured to rotationally lock a plunger rod guide nut when the proximal part and the distal part are connected to each other.

10. The metered droplet medicament delivery device of claim 7, wherein the dose delivery mechanism further comprises a plunger rod guide nut rotationally locked relative to the plunger rod, and a drive nut threadedly connected to the plunger rod that is rotatable in the distal part such that the plunger rod is rotatable and thereby is movable in a distal direction when in engagement with the plunger rod positioning cap.

11. The metered droplet medicament delivery device of claim 10, wherein the dose delivery mechanism further comprises:
    a rotatable drive member drivingly connected to the drive nut;
    a spring force member having a first end connected to the drive member and a second end connected to a fixed point on a chassis;
    a spring force tensioning mechanism operably connected to the spring force member to tension the spring force member before dose delivery; and an activation mechanism releasably interconnected to the drive member by an engagement mechanism for rotationally locking the drive member when the spring force member is tensioned, wherein operation of the activation mechanism releases the drive member and the spring force member, whereby the drive member drives the dose delivery mechanism for delivery of a dose of medicament.

12. The metered droplet medicament delivery device of claim 7, wherein the plunger rod positioning cap comprises a seat for the proximal end of the plunger rod, and a contact surface for contacting the distal part.

13. The metered droplet medicament delivery device of claim 12, wherein the proximal part comprises a plunger rod guide nut lock member configured to rotationally lock a plunger rod guide nut when the proximal part and the distal part are connected to each other.

14. The metered droplet medicament delivery device of claim 12, wherein the dose delivery mechanism further comprises a plunger rod guide nut rotationally locked relative to the plunger rod, and a drive nut threadedly connected to the plunger rod that is rotatable in the distal part such that the plunger rod is rotatable and thereby is movable in a distal direction when in engagement with the plunger rod positioning cap.

15. The metered droplet medicament delivery device of claim 14, wherein the dose delivery mechanism further comprises:
a rotatable drive member drivingly connected to the drive nut;
a spring force member having a first end connected to the drive member and a second end connected to a fixed point on a chassis;
a spring force tensioning mechanism operably connected to the spring force member to tension the spring force member before dose delivery; and
an activation mechanism releasably interconnected to the drive member by an engagement mechanism for rotationally locking the drive member when the spring force member is tensioned, wherein operation of the activation mechanism releases the drive member and the spring force member, whereby the drive member drives the dose delivery mechanism for delivery of a dose of medicament.

16. The metered droplet medicament delivery device of claim 12, further comprising first holding members on the plunger rod positioning cap that cooperate with corresponding second holding members on the distal part for releasably holding the plunger rod positioning cap.

17. The metered droplet medicament delivery device of claim 16, wherein the dose delivery mechanism further comprises a plunger rod guide nut rotationally locked relative to the plunger rod, and a drive nut threadedly connected to the plunger rod that is rotatable in the distal part such that the plunger rod is rotatable and thereby is movable in a distal direction when in engagement with the plunger rod positioning cap.

18. The metered droplet medicament delivery device of claim 17, wherein the proximal part comprises a plunger rod guide nut lock member configured to rotationally lock the plunger rod guide nut when the proximal part and the distal part are connected to each other.

19. The metered droplet medicament delivery device of claim 17, wherein the dose delivery mechanism further comprises:
a rotatable drive member drivingly connected to the drive nut;
a spring force member having a first end connected to the drive member and a second end connected to a fixed point on a chassis;
a spring force tensioning mechanism operably connected to the spring force member to tension the spring force member before dose delivery; and
an activation mechanism releasably interconnected to the drive member by an engagement mechanism for rotationally locking the drive member when the spring force member is tensioned, wherein operation of the activation mechanism releases the drive member and the spring force member, whereby the drive member drives the dose delivery mechanism for delivery of a dose of medicament.

\* \* \* \* \*